US011845928B2

(12) United States Patent
Zhu et al.

(10) Patent No.: US 11,845,928 B2
(45) Date of Patent: Dec. 19, 2023

(54) METHODS AND KITS FOR FRAGMENTING DNA

(71) Applicant: Tsinghua University, Beijing (CN)

(72) Inventors: Ting Zhu, Beijing (CN); Yuval Ebenstein, Yavne (IL); Chunbo Lou, Beijing (CN); Wenjun Jiang, Beijing (CN); Xuejin Zhao, Beijing (CN); Tslil Gabrieli, Ramat-Yishai (IL)

(73) Assignee: Tsinghua University, Beijing (CN)

( * ) Notice: Subject to any disclaimer, the term of this patent is extended or adjusted under 35 U.S.C. 154(b) by 0 days.

(21) Appl. No.: 15/557,502

(22) PCT Filed: Apr. 14, 2016

(86) PCT No.: PCT/IL2016/050394
§ 371 (c)(1),
(2) Date: Sep. 12, 2017

(87) PCT Pub. No.: WO2016/178207
PCT Pub. Date: Nov. 10, 2016

(65) Prior Publication Data
US 2018/0044659 A1    Feb. 15, 2018

Related U.S. Application Data

(60) Provisional application No. 62/156,417, filed on May 4, 2015.

(51) Int. Cl.
*C12N 15/10* (2006.01)
*C12Q 1/6806* (2018.01)
*C12Q 1/6869* (2018.01)

(52) U.S. Cl.
CPC ....... *C12N 15/1003* (2013.01); *C12N 15/101* (2013.01); *C12Q 1/6806* (2013.01); *C12Q 1/6869* (2013.01)

(58) Field of Classification Search
CPC .. C12N 15/1003; C12N 15/101; C12N 15/11; C12Q 1/6806; C12Q 1/6869;
(Continued)

(56) References Cited

U.S. PATENT DOCUMENTS 5,185,071 A * 2/1993 Serwer ............. G01N 27/44756
204/457
5,427,664 A * 6/1995 Stoev ................. G01N 15/0272
204/462
(Continued)

FOREIGN PATENT DOCUMENTS

WO    WO 01/62974     8/2001
WO    WO 2010/102257  9/2010
(Continued)

OTHER PUBLICATIONS

Gibson et al. Nature Methods. 2009. 6:343-345. (Year: 2009).*
(Continued)

*Primary Examiner* — Joseph G. Dauner

(57) ABSTRACT

A method of DNA fragmentation is provided. The method comprising incubating a semi-solid biological sample which comprises the DNA with an auxiliary domain-directed nuclease having a binding affinity and selectivity to predefined sites in the DNA so as to yield a DNA fragment-of-interest, to thereby fragment the DNA.

12 Claims, 5 Drawing Sheets
(3 of 5 Drawing Sheet(s) Filed in Color)
Specification includes a Sequence Listing.

(58) Field of Classification Search
CPC ............ C12Q 2521/301; C12Q 12/682; C12Q 2525/307; C12Q 2531/125; C12Q 2561/125
See application file for complete search history.

(56) References Cited

U.S. PATENT DOCUMENTS

| | | | | |
|---|---|---|---|---|
| 5,460,941 | A * | 10/1995 | Camerini-Otero ... | C12N 15/113 435/91.1 |
| 5,545,806 | A * | 8/1996 | Lonberg ............. | A01K 67/0276 424/184.1 |
| 5,789,167 | A * | 8/1998 | Konrad ................. | C12Q 1/68 435/6.11 |
| 6,391,642 | B1 * | 5/2002 | Resnick ................ | C12N 15/81 435/320.1 |
| 6,444,421 | B1 * | 9/2002 | Chung ................. | C12Q 1/6813 435/455 |
| 6,869,596 | B1 * | 3/2005 | Knowland ............ | A61K 8/11 106/286.4 |
| 2001/0033848 | A1 * | 10/2001 | Jacobson ............ | A61K 2300/00 424/401 |
| 2003/0049675 | A1 * | 3/2003 | Nalin ............... | G01N 27/44773 435/6.12 |
| 2004/0180350 | A1 * | 9/2004 | Nalin ................. | C12N 15/1027 435/6.14 |
| 2006/0015949 | A1 * | 1/2006 | Lonberg .............. | C07K 16/462 800/6 |
| 2010/0209998 | A1 * | 8/2010 | Attwood ............. | C07K 14/005 435/252.3 |
| 2013/0217612 | A1 * | 8/2013 | Altermann ........ | A61K 39/0001 514/1.1 |
| 2014/0068797 | A1 * | 3/2014 | Doudna ................ | C12Q 1/686 435/375 |
| 2014/0287468 | A1 | 9/2014 | Richard | |
| 2014/0349405 | A1 * | 11/2014 | Sontheimer ........... | C12N 15/85 435/325 |
| 2014/0357523 | A1 | 12/2014 | Zeiner et al. | |

FOREIGN PATENT DOCUMENTS

| | | | | |
|---|---|---|---|---|
| WO | WO-2013126794 | A1 * | 8/2013 | ............ A61K 38/465 |
| WO | WO 2013/142578 | | 9/2013 | |
| WO | WO-2014071235 | A1 * | 5/2014 | ............ C12N 15/113 |
| WO | WO 2016/178207 | | 11/2016 | |

OTHER PUBLICATIONS

Figure 1:
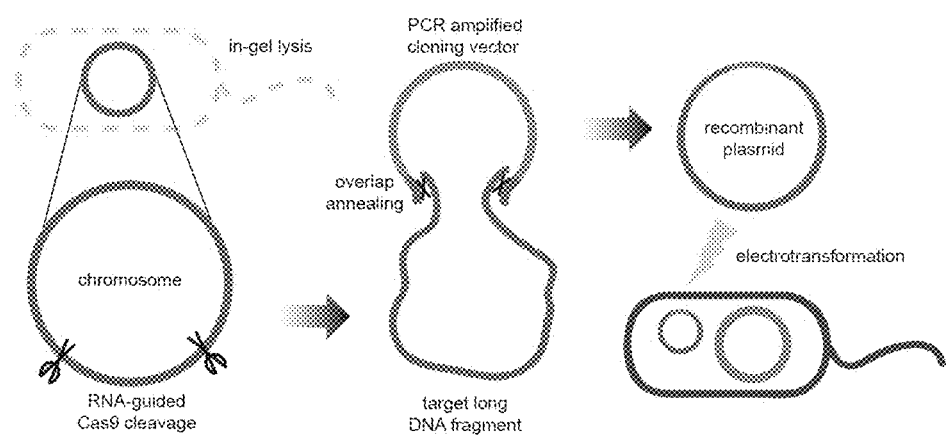

Mandal et al. Cell Stem Cell. 2014. 15:643-652 and Supplemental Information. (Year: 2014).*
Stemcell. Retrieved on Jul. 9, 2019 from the internet: https://www.stemcell.com/media/files/manual/MA28404-Human_Colony_Forming_Unit_Assays_Using_MethoCult.pdf). (Year: 2019).*
Jiang et al. Nat Biotechnology. 2013. 31(3):233-239. (Year: 2013).*
Karvelis et al. Biochem Soc Trans. 2013. 41:1401-1406. (Year: 2013).*
Asegame et al. International Journal of Genetics and Molecular Biology. 2010. 2(10):202-206. (Year: 2010).*
IDT—Molecular Facts and Figures. Retrieved on Aug. 27, 2020 from the internet: https://www.interchim.fr/ft/4/47255g.pdf. (Year: 2020).*
ThermoScientific—Digestion of agarose-embedded DNA. Retreived on Aug. 27, 2020 from the internet: https://assets.thermofisher.com/TFS-Assets/LSG/manuals/digest_agarose_embedded_DNA.pdf. (Year: 2020).*
Cas9 S. Pyogenes. Retrieved on Aug. 27, 2020 from the internet: https://www.prospecbio.com/cas9_s_pyogenes. (Year: 2020).*
Cas9 Nuclease. Retrieved on Aug. 27, 2020 from the internet: https://www.mclab.com/Cas9-Nuclease.html. (Year: 2020).*
IDT—Restriction Endonucleases. Retrieved on Aug. 27, 2020 from the internet: https://sfvideo.blob.core.windows.net/sitefinity/docs/default-source/biotech-basics/restriction-endonucleases.pdf?sfvrsn=1e563407_4. (Year: 2020).*
Protein Electrophoresis in Agarose Gels. Retrieved on Aug. 27, 2020 from the internet: https://www.interchim.fr/ft/4/47255g.pdf (Year: 2020).*
Gardner et al. Immunology. 1969. 17:71. (Year: 1969).*
Hornbeck et al. Current Protocols in Immunology. 1991. 2.3.1-2.3.4. (Year: 1991).*
Antibody Basics. Retrieved on Feb. 17, 2021 from the internet: https://www.sigmaaldrich.com/technical-documents/articles/biology/antibody-basics.html. (Year: 2021).*
Fatin-Rouge et al. Biophysical Journal. 2004. 86:2710-2719. (Year: 2004).*
Boyer et al. AIChE Journal. 1992. 38(2):259-272. (Year: 1992).*
Wunderly et al. Nature. 1960. 186:885-886 (Year: 1960).*
Lee et al. Nucleic Acids Research. 2015. 43(8):e55. (Year: 2015).*
Kouprina et al. Methods Mol. Biol. 2004. 255: 69-89. (Year: 2004).*
Kouprina et al. PLOS Biology. 2004. 2(5):0653-0663. (Year: 2004).*
Sweeney. "Proteinase K (EC 3.4.21.14)" from Methods in Molecular Biology, vol. 16: Enzymes of Molecular Biology. 1993. (Year: 1993).*
Wiegers et al. Biochemical and Biophysical Research Communications. 1971. 44(2):513-519. (Year: 1971).*
Hendel et al. Nature Biotechnology. 2015. 33(9):985-989 and Online Methods. (Year: 2015).*
Yue et al. Nanoscale. 2018. 10:1063-1071. (Year: 2018).*
Supplementary European Search Report and the European Search Opinion dated Sep. 17, 2018 From the European Patent Office Re. Application No. 16789403.9. (10 Pages).
Grozdanov et al. "Generation of Plasmid Vectors Expressing FLAG-Tagged Proteins Under the Regulation of Human Elongation Factor-1 Alpha Promoter Using Gibson Assembly", Journal of Visualized Experiments, XP055505256, 96: e52235-1-e52235-10, Published Online Feb. 9, 2015. Abstract.
Sambrook et al. "Recovery of DNA From Low-Melting-Temperature Agarose Gels: Enzymatic Digestion With Agarase", Cold Spring Harbor Protocols, XP055505022, 2006(1): 1-2 , Jun. 2006.
Wang et al. "CRISPR/Cas 9 Nuclease Cleavage Combined With Gibson Assembly for Seamless Cloning", Biotechniques, XP055385711, 58(4): 161-170, Apr. 2015. Fig.1.
Zhang et al. "Preparation of Megabase-Size DNA From Plant Nuclei", The Plant Journal, XP055505187, 7(1): 175-184, Jan. 1995. p. 177, col. 1, Last Para, p. 178, Fig.4.
International Search Report and the Written Opinion dated Jun. 30, 2016 From the International Searching Authority Re. Application No. PCT/IL2016/050394.
Birren et al. "Restriction Enzyme Digestion of Large DNA Fragments in Agarose", Pulsed Field Gel Electrophoresis: A Practical Guide, 1st Ed., Chap.5: 88-90, Mar. 28, 1993. p. 87-88, Table 5.1.
Jiang et al. "Cas9-Assisted Targeting of Chromosome Segments CATCH Enables One-Step Targeted Cloning of Large Gene Clusters", Nature Communications, 6: 8101-1-8101-8, Sep. 1, 2015.
Jiang et al. "Targeted Isolation and Cloning of 100-Kb Microbial Genomic Sequences by Cas9-Assisted Targeting of Chromosome Segments", Nature Protocols, 11(5): 960-975, Published Online Apr. 21, 2016.
Lee et al. "Highly Efficient CRISPR/Cas9-Mediated TAR Cloning of Genes and Chromosomal Loci From Complex Genomes in Yeast", Nucleic Acids Research, 43(8): e55-1-e55-9, Published Online Feb. 17, 2015. p. 3, Right col. Last Para—p. 4, Left col., First Para.
Communication Pursuant to Article 94(3) EPC dated Jul. 31, 2019 From the European Patent Office Re. Application No. 16789403.9. (1 Page).
Liles et al. "Recovery, Purification, and Cloning of High-Molecular-Weight DNA From Soil Microorganisms", Applied and Environmental Microbiology, XP055608979, 74(10): 3302-3305, Published Ahead of Print Mar. 21, 2008.
Sternberg et al. "DNA Interrogation by the CRISPR RNA-Guided Endonuclease Cas9", Nature, 507(7490): 62-67, Mar. 6, 2014.
Wing et al. "An Improved Method of Plant Megabase DNA Isolation in Agarose Microbeads Suitable for Physical Mapping and YAC Cloning", The Plant Journal, 4(5): 893-898, Nov. 1993.

(56) References Cited

OTHER PUBLICATIONS

Notification of Office Action and Search Report dated Jun. 1, 2021 From the State Intellectual Property Office of the People's Republic of China Re. Application No. 201680039772.3 and Its Translation of Office Action Into English. (18 Pages).
Zhang et al. "Physical Chemistry", China Medical Science and Technology Press, p. 304-307, Aug. 2014.

* cited by examiner

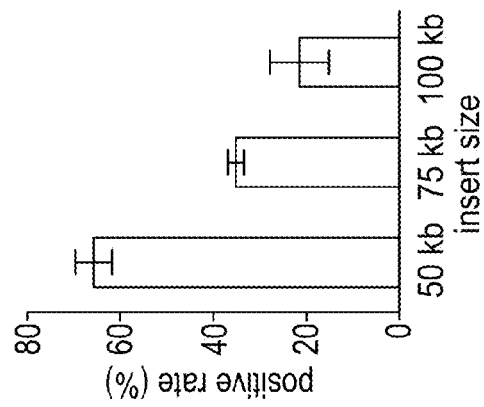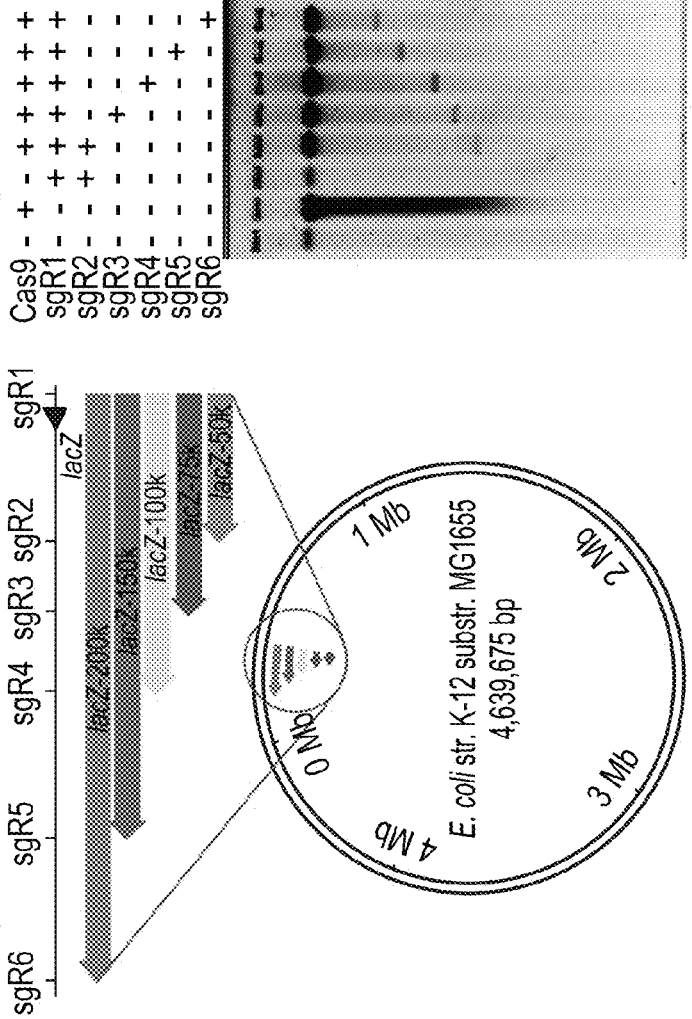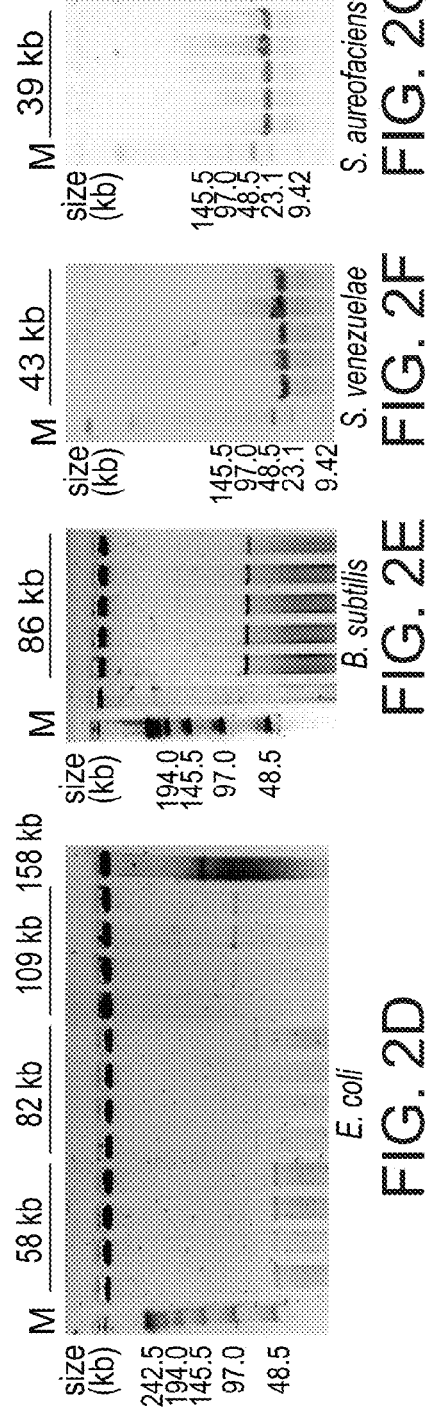

SEQUENCE LISTING

```
<160> NUMBER OF SEQ ID NOS: 44

<210> SEQ ID NO 1
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 1
gttttagagc tagaaatagc aagttaaaat aaggctagtc                          40

<210> SEQ ID NO 2
<211> LENGTH: 59
<212> TYPE: DNA
<213> ORGANISM: Artificial sequence
<220> FEATURE:
<223> OTHER INFORMATION: Single strand DNA oligonucleotide

<400> SEQUENCE: 2
aaaagcaccg actcggtgcc acttttcaa gttgataacg gactagcctt attttaact     59

<210> SEQ ID NO 3
<211> LENGTH: 59
<212> TYPE: DNA
<213> ORGANISM: Artificial sequence
<220> FEATURE:
<223> OTHER INFORMATION: Single strand DNA oligonucleotide

<400> SEQUENCE: 3
taatacgact cactataggt gcggatatct cggtagtgtt ttagagctag aaatagcaa    59

<210> SEQ ID NO 4
<211> LENGTH: 59
<212> TYPE: DNA
<213> ORGANISM: Artificial sequence
<220> FEATURE:
<223> OTHER INFORMATION: Single strand DNA oligonucleotide

<400> SEQUENCE: 4
taatacgact cactataggt aggatcataa agtcctcgtt ttagagctag aaatagcaa    59

<210> SEQ ID NO 5
```

```
<211> LENGTH: 58
<212> TYPE: DNA
<213> ORGANISM: Artificial sequence
<220> FEATURE:
<223> OTHER INFORMATION: Single strand DNA oligonucleotide

<400> SEQUENCE: 5
taatacgact cactatagaa tctgtcgccg aagtaaagtt ttagagctag aaatagca      58

<210> SEQ ID NO 6
<211> LENGTH: 55
<212> TYPE: DNA
<213> ORGANISM: Artificial sequence
<220> FEATURE:
<223> OTHER INFORMATION: Single strand DNA oligonucleotide

<400> SEQUENCE: 6
taatacgact cactatagct gtcggggtga atttgctgtt ttagagctag aaata         55

<210> SEQ ID NO 7
<211> LENGTH: 55
<212> TYPE: DNA
<213> ORGANISM: Artificial sequence
<220> FEATURE:
<223> OTHER INFORMATION: Single strand DNA oligonucleotide

<400> SEQUENCE: 7
taatacgact cactatagta aatctgggga tggcgctgtt ttagagctag aaata         55

<210> SEQ ID NO 8
<211> LENGTH: 58
<212> TYPE: DNA
<213> ORGANISM: Artificial sequence
<220> FEATURE:
<223> OTHER INFORMATION: Single strand DNA oligonucleotide

<400> SEQUENCE: 8
taatacgact cactatagta aacagctgca atcccatgtt ttagagctag aaatagca      58

<210> SEQ ID NO 9
<211> LENGTH: 58
<212> TYPE: DNA
<213> ORGANISM: Artificial sequence
<220> FEATURE:
<223> OTHER INFORMATION: Single strand DNA oligonucleotide

<400> SEQUENCE: 9
taatacgact cactatagcc tatgagattc ctttattgtt ttagagctag aaatagca      58

<210> SEQ ID NO 10
<211> LENGTH: 61
<212> TYPE: DNA
<213> ORGANISM: Artificial sequence
<220> FEATURE:
<223> OTHER INFORMATION: Single strand DNA oligonucleotide

<400> SEQUENCE: 10
taatacgact cactataggc gaagtccttg cccatgatgg ttttagagct agaaatagca    60
a                                                                    61

<210> SEQ ID NO 11
<211> LENGTH: 61
<212> TYPE: DNA
<213> ORGANISM: Artificial sequence
<220> FEATURE:
<223> OTHER INFORMATION: Single strand DNA oligonucleotide
```

<400> SEQUENCE: 11
taatacgact cactatagga cgacgaggat ccgacctgag tttagagct agaaatagca    60 a                                                                  61

<210> SEQ ID NO 12
<211> LENGTH: 60
<212> TYPE: DNA
<213> ORGANISM: Artificial sequence
<220> FEATURE:
<223> OTHER INFORMATION: Single strand DNA oligonucleotide

<400> SEQUENCE: 12
taatacgact cactatagga cccaccggag gacttcgcag tttagagct agaaatagca    60

<210> SEQ ID NO 13
<211> LENGTH: 57
<212> TYPE: DNA
<213> ORGANISM: Artificial sequence
<220> FEATURE:
<223> OTHER INFORMATION: Single strand DNA oligonucleotide

<400> SEQUENCE: 13
taatacgact cactataggt ctccaccgtc taccgcgacg tttagagct agaaata       57

<210> SEQ ID NO 14
<211> LENGTH: 59
<212> TYPE: DNA
<213> ORGANISM: Artificial sequence
<220> FEATURE:
<223> OTHER INFORMATION: Single strand DNA oligonucleotide

<400> SEQUENCE: 14
tgagctgtct tcggtatcgt cgtatcccac tttattatca cttattcagg cgtagcaac    59

<210> SEQ ID NO 15
<211> LENGTH: 50
<212> TYPE: DNA
<213> ORGANISM: Artificial sequence
<220> FEATURE:
<223> OTHER INFORMATION: Single strand DNA oligonucleotide

<400> SEQUENCE: 15
gacatgccaa aagagtggac aacgacccga ggcggccgca tcgaatataa               50

<210> SEQ ID NO 16
<211> LENGTH: 54
<212> TYPE: DNA
<213> ORGANISM: Artificial sequence
<220> FEATURE:
<223> OTHER INFORMATION: Single strand DNA oligonucleotide

<400> SEQUENCE: 16
gccgtttcaa atctaacact cgtaatttac cctttgcggc cgcatcgaat ataa          54

<210> SEQ ID NO 17
<211> LENGTH: 50
<212> TYPE: DNA
<213> ORGANISM: Artificial sequence
<220> FEATURE:
<223> OTHER INFORMATION: Single strand DNA oligonucleotide

<400> SEQUENCE: 17
agcaacgact gatagtagta tcttccccag cgcggccgca tcgaatataa               50

<210> SEQ ID NO 18
<211> LENGTH: 50
<212> TYPE: DNA
<213> ORGANISM: Artificial sequence
<220> FEATURE:
<223> OTHER INFORMATION: Single strand DNA oligonucleotide

<400> SEQUENCE: 18
ttttgctgcc accagatttg cgccgcccga cgcggccgca tcgaatataa         50

<210> SEQ ID NO 19
<211> LENGTH: 59
<212> TYPE: DNA
<213> ORGANISM: Artificial sequence
<220> FEATURE:
<223> OTHER INFORMATION: Single strand DNA oligonucleotide

<400> SEQUENCE: 19
gttttcttgg tgaatatgaa gctcacctaa tttattatca cttattcagg cgtagcaac     59

<210> SEQ ID NO 20
<211> LENGTH: 50
<212> TYPE: DNA
<213> ORGANISM: Artificial sequence
<220> FEATURE:
<223> OTHER INFORMATION: Single strand DNA oligonucleotide

<400> SEQUENCE: 20
taccgcggag cctcagcgac cgcagcccat ggcggccgca tcgaatataa         50

<210> SEQ ID NO 21
<211> LENGTH: 59
<212> TYPE: DNA
<213> ORGANISM: Artificial sequence
<220> FEATURE:
<223> OTHER INFORMATION: Single strand DNA oligonucleotide

<400> SEQUENCE: 21
agtgccacaa gcgtctaggg gagctccaca tggtgaagat cctttttgat aatctcatg    59

<210> SEQ ID NO 22
<211> LENGTH: 58
<212> TYPE: DNA
<213> ORGANISM: Artificial sequence
<220> FEATURE:
<223> OTHER INFORMATION: Single strand DNA oligonucleotide

<400> SEQUENCE: 22
cggcggaggt gccgtggaag ccgggccgtc atagatcctt ttggttcatg tgcagctc     58

<210> SEQ ID NO 23
<211> LENGTH: 59
<212> TYPE: DNA
<213> ORGANISM: Artificial sequence
<220> FEATURE:
<223> OTHER INFORMATION: Single strand DNA oligonucleotide

<400> SEQUENCE: 23
gcctctggcc ggccggggaa agcagccatg cggtgaagat cctttttgat aatctcatg    59

<210> SEQ ID NO 24
<211> LENGTH: 58
<212> TYPE: DNA
<213> ORGANISM: Artificial sequence
<220> FEATURE:
<223> OTHER INFORMATION: Single strand DNA oligonucleotide

<400> SEQUENCE: 24
gcaggtgggt gagggtgtcg gtcatcccgt ctagatcctt ttggttcatg tgcagctc    58

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 25
agtccgagct catcgctaat    20

<210> SEQ ID NO 26
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 26
ggatagtgtt caccctttgtt aca    23

<210> SEQ ID NO 27
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 27
gcattttgat tcacagcagt ca    22

<210> SEQ ID NO 28
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 28
gacgataacc ttagagggat gat    23

<210> SEQ ID NO 29
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 29
cgagctttaa tgcctctgct    20

<210> SEQ ID NO 30
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 30
attcctgtgc cttaatgaca at    22

<210> SEQ ID NO 31

```
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 31
ccatacaatc atcgtatcgg gt                                              22

<210> SEQ ID NO 32
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 32
ccctccatcc ctcgttctaa                                                 20

<210> SEQ ID NO 33
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 33
gagtccaacc cggtaagaca cgac                                            24

<210> SEQ ID NO 34
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 34
gagcgtccct cccggacc                                                   18

<210> SEQ ID NO 35
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 35
acggacgaga tccacacgg                                                  19

<210> SEQ ID NO 36
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 36
tcgccctggc cctggacag                                                  19

<210> SEQ ID NO 37
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 37
```

```
gaccgagagc gcggccacc                                                    19

<210> SEQ ID NO 38
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 38
tggcgacagg cgcgagtga                                                    19

<210> SEQ ID NO 39
<211> LENGTH: 55
<212> TYPE: DNA
<213> ORGANISM: Artificial sequence
<220> FEATURE:
<223> OTHER INFORMATION: Single strand DNA oligonucleotide

<400> SEQUENCE: 39
taatacgact cactatagct gtttacctat aatagtcgtt ttagagctag aaata            55

<210> SEQ ID NO 40
<211> LENGTH: 59
<212> TYPE: DNA
<213> ORGANISM: Artificial Sequence
<220> FEATURE:
<223> OTHER INFORMATION: Single strand DNA oligonucleotide

<400> SEQUENCE: 40
taatacgact cactataggg caaaaatgcc gaagatggtt ttagagctag aaatagcaa        59

<210> SEQ ID NO 41
<211> LENGTH: 59
<212> TYPE: DNA
<213> ORGANISM: Artificial Sequence
<220> FEATURE:
<223> OTHER INFORMATION: Single strand DNA oligonucleotide

<400> SEQUENCE: 41
taatacgact cactatagga tatcgccgga gtcctcggtt ttagagctag aaatagcaa        59

<210> SEQ ID NO 42
<211> LENGTH: 59
<212> TYPE: DNA
<213> ORGANISM: Artificial Sequence
<220> FEATURE:
<223> OTHER INFORMATION: yeast-sgR1-P

<400> SEQUENCE: 42
taatacgact cactataggg tctggaatgg tacagttgtt ttagagctag aaatagcaa        59

<210> SEQ ID NO 43
<211> LENGTH: 59
<212> TYPE: DNA
<213> ORGANISM: Artificial Sequence
<220> FEATURE:
<223> OTHER INFORMATION: yeast-sgR2-P

<400> SEQUENCE: 43
taatacgact cactataggg tctggaatgg tacagttgtt ttagagctag aaatagcaa        59

<210> SEQ ID NO 44
<211> LENGTH: 59
<212> TYPE: DNA
```

```
<213> ORGANISM: Artificial Sequence
<220> FEATURE:
<223> OTHER INFORMATION: yeast-sgR3-P

<400> SEQUENCE: 44
taatacgact cactatagac caagctaaac aattattgtt ttagagctag aaatagcaa    59
```

METHODS AND KITS FOR FRAGMENTING DNA

RELATED APPLICATIONS

This application is a National Phase of PCT Patent Application No. PCT/IL2016/050394 having International filing date of Apr. 14, 2016, which claims the benefit of priority under 35 USC § 119(e) of U.S. Provisional Patent Application No. 62/156,417 filed on May 4, 2015. The contents of the above applications are all incorporated by reference as if fully set forth herein in their entirety.

SEQUENCE LISTING STATEMENT

The ASCII file, entitled 70724SequenceListing.txt, created on Sep. 12, 2017, comprising 9,621 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to methods and kits for fragmenting DNA which can be further employed in DNA sequencing, imaging, amplification and cloning.

The cloning of long genomic sequences, especially those containing large gene clusters, is of particular importance to synthetic biology and genetic engineering efforts to produce pharmaceuticals and biofuels. Traditional PCR-based cloning methods are often limited by length and GC content of the DNA template: standard PCR reactions routinely yield fragments of up to 10 kb, while longer PCR products require tedious optimization of reaction conditions and, even under ideal conditions, are typically limited to 35 kb[5]. Alternatively, one may generate long genomic sequences of interest through the assembly of multiple short fragments, such as overlapping PCR products or chemically synthesized DNA oligos, although such methods tend to be time-consuming and expensive, particularly for obtaining sequences longer than 50 kb (which typically require 3-5 stages, each containing multiple assembly events)[6,7]. Another route to obtain long genomic sequences is by restriction enzyme digestion of genomic DNA. However, being a non-targeted approach, selecting a specific sequence of interest from a vast number of restriction digest products can be intensely challenging and cumbersome[8]. Certain techniques, such as transformation-associated recombination[9,10] and single-strand overlapping annealing[11] have been developed to clone specific, large bacterial gene clusters. Nevertheless, the utility of these techniques remains limited because they rely on the availability of unique restriction sites that flank the target genomic region and often the presence of selection markers in the target sequence. To facilitate advancements in biotechnology and synthetic biology, it is imperative to develop a general approach to clone near-arbitrary, long genomic sequences that are difficult to obtain using conventional methods. Similarly, isolation of such near-arbitrary, long genomic sequences will enable genomic applications that specifically target these regions such as ultra-deep or multiplexed next generation sequencing, optical DNA mapping and other targeted genomics applications.

CRISPR-Cas9, originally discovered as a component of the *Streptococcus pyogenes* adaptive immune system, harbors the Cas9 endonuclease that can be directed by guide RNAs to cleave specific sequences[12]. Its long, programmable recognition site (20 bp) results in much higher targeting specificity and versatility than those of traditional restriction enzymes (with fixed recognition sites limited to 6-8 bp), which has motivated extensive development of Cas9-based genome editing in vivo[13]. In contrast, the potential applications of the Cas9 system in vitro have not yet been well-explored; instead, they mainly focused on testing the enzyme's cleavage efficiency and sequence-recognition specificity or handling short sequences[14,15].

Additional Background Art Includes:
WO2013142578
US20140357523

SUMMARY OF THE INVENTION

According to an aspect of some embodiments of the present invention there is provided a method of fragmenting DNA, the method comprising, incubating a semi-solid biological sample which comprises the DNA with an auxiliary domain-directed nuclease having a binding affinity and selectivity to pre-defined sites in the DNA so as to yield a DNA fragment-of-interest, to thereby fragment the DNA.

According to an aspect of some embodiments of the present invention there is provided a method of cloning, the method comprising:

(a) fragmenting a DNA as described herein, so as to obtain at least one DNA fragment-of-interest; and (b) cloning the DNA fragment-of-interest.

According to some embodiments of the invention, the method further comprises melting the semi-solid biological sample following the fragmenting and prior to the cloning.

According to an aspect of some embodiments of the present invention there is provided a method of DNA sequencing, the method comprising:

(a) fragmenting a DNA as described herein, so at to obtain at least one DNA fragment-of-interest;

(b) separating the DNA fragment-of-interest from the DNA; and (c) sequencing the DNA fragment-of-interest.

According to an aspect of some embodiments of the present invention there is provided a method of nucleic acid amplification, the method comprising:

(a) fragmenting a DNA as described herein, so at to obtain at least one DNA fragment-of-interest;

(b) separating the DNA fragment-of-interest from the DNA; and (c) amplifying the DNA fragment-of-interest.

According to an aspect of some embodiments of the present invention there is provided a method of in situ imaging DNA, the method comprising:

(a) fragmenting a DNA as described herein, so at to obtain at least one DNA fragment-of-interest;

(b) separating the DNA fragment-of-interest from the DNA;

(c) attaching a labeling agent to the DNA fragment-of-interest; and (d) subjecting the DNA fragment-of-interest to an imaging method suitable for detecting the labeling agent.

According to some embodiments of the invention, the DNA fragment-of-interest is 50-150 kb in length.

According to some embodiments of the invention, the DNA is genomic DNA.

According to some embodiments of the invention, the DNA is human DNA.

According to some embodiments of the invention, the DNA is chromosomal DNA.

According to some embodiments of the invention, the DNA fragment-of-interest comprises a gene cluster.

According to some embodiments of the invention, the semi-solid biological sample is in a form of a gel.

According to some embodiments of the invention, the semi-solid biological sample prevents DNA shearing.

According to some embodiments of the invention, the separating the DNA fragment-of-interest from the DNA is effected by at least one of:
(a) melting the semi-solid biological sample; and
(b) subjecting the semi-solid biological sample to enzymatic treatment which digests the gel matrix of the semi-solid biological sample.

According to some embodiments of the invention, separating the DNA fragment-of-interest from the DNA comprises pulsed-field gel electrophoresis.

According to some embodiments of the invention, the cloning is effected by Gibson assembly.

According to some embodiments of the invention, the method further comprises providing cells which comprise the chromosomal DNA and lysing the cells in the semi-solid biological sample prior to the fragmenting. According to some embodiments of the invention, the method further comprises assessing fragmentation efficiency of the DNA following the fragmenting.

According to some embodiments of the invention, the assessing fragmentation efficiency is effected by pulsed-field gel electrophoresis.

According to an aspect of some embodiments of the present invention there is provided a kit for DNA fragmentation, the kit comprising:
(i) a first container comprising an auxiliary domain-directed nuclease;
(ii) a second container comprising low melting gel matrix; and optionally
(iii) a third container comprising a cell lysis buffer.

According to an aspect of some embodiments of the present invention there is provided a kit for DNA cloning, the kit comprising the components as described hereinabove and further a container comprising an exonuclease for Gibson assembly.

According to an aspect of some embodiments of the present invention there is provided a kit for DNA amplification, the kit comprising the components as described hereinabove and a further container comprising a polymerase.

According to some embodiments of the invention, the kit comprising the components described hereinabove and a further container comprising a labeling agent.

According to some embodiments of the invention, the auxiliary domain-directed nuclease is an oligonucleotide-directed nuclease.

According to some embodiments of the invention, the oligonucleotide-directed nuclease is selected from the group consisting of a Cas and a RISC.

According to some embodiments of the invention, the Cas comprises Cas-9.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a scheme One-step large-gene-cluster cloning by the CRISPR-Cas9-Assisted Targeting of CHromosome segments (CATCH). After in-gel lysis of bacterial cells, the chromosomes are cleaved by RNA-guided Cas9 at the designated target sites. A cloning vector (length not to scale) that shares 30 bp terminal sequences overlaps (black cross) with the target DNA at both ends is ligated to the target fragment in a Gibson assembly mix. The recombinant plasmid is then electrotransformed into a cloning host.

FIGS. 2A-G depict the cloning of long genomic sequences of variable lengths by CATCH. FIG. 2A—A total of 5 sgRNA pairs (SEQ ID NOs: 3-13) were designed to target fragments of different lengths (50, 75, 100, 150, and 200 kb, respectively) in the *E. coli* genome, all containing a *lacZ* gene. FIG. 2B—*E. coli* chromosomes in agarose gel plug were digested by Cas9 with the corresponding sgRNA pairs and analyzed by PFGE. FIG. 2C—The positive rates of CATCH cloning with different insert sizes (50-100 kb; only 1 positive clone was obtained with the 150 kb insert and none with 200 kb). FIG. 2D—Plasmids carrying the target sequences cloned from *E. coli* were purified from the blue-white-screening- and PCR- positive clones, linearized, and analyzed by PFGE. FIGS. 2E-G—Plasmids carrying the target large gene clusters cloned from *B. subtilis, S. venezuelae,* or *S. aureofaciens,* respectively, were purified from the PCR-positive clones, linearized, and analyzed by PFGE. M, marker.

Figure 3:
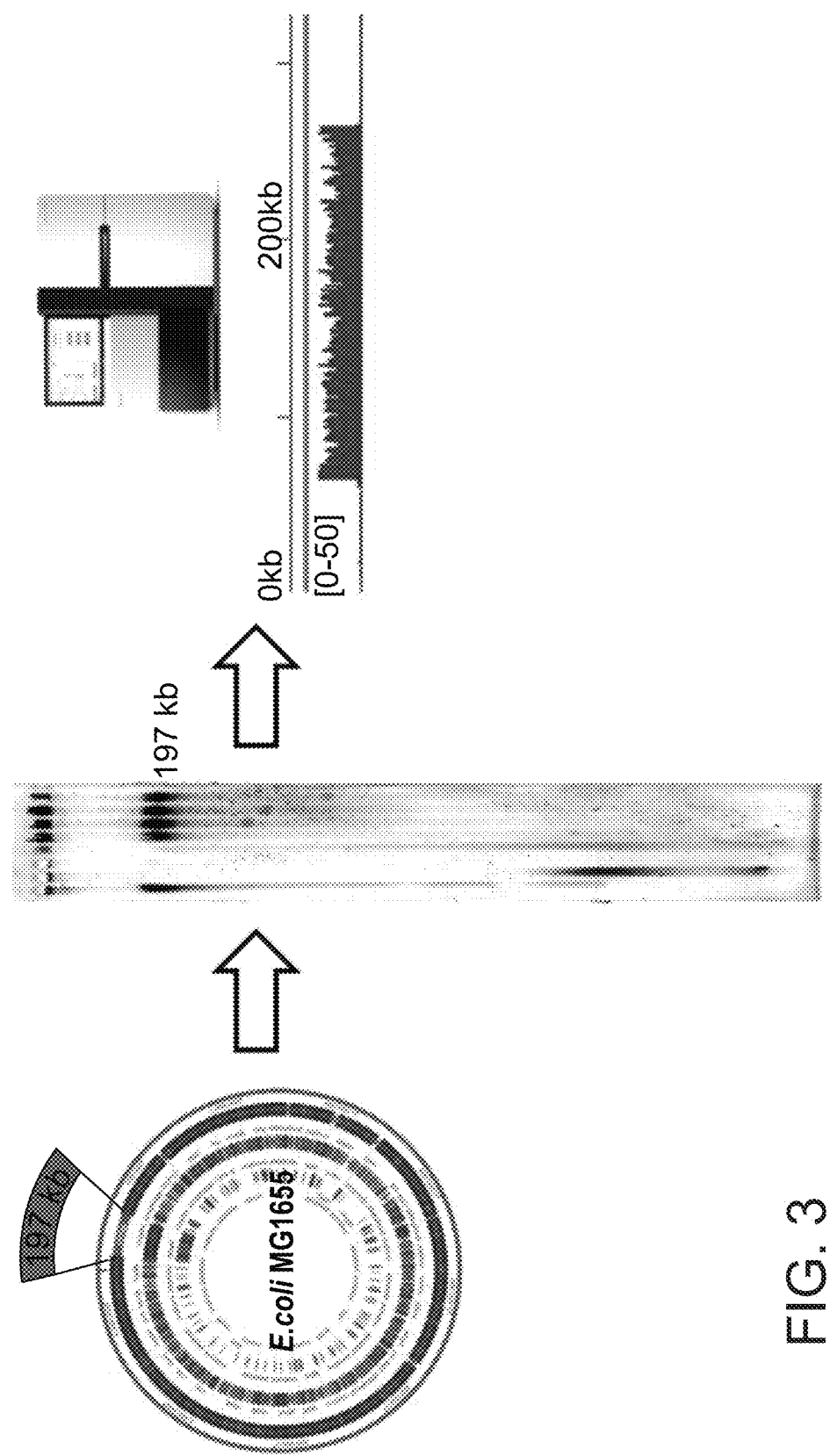

FIG. 3 depicts the results for targeted sequencing in *E. coli*. A 197 kb genomic region has been selected and cleaved "in-gel" as described above. The gel plug containing the fragmented genomic material is placed in the well of an agarose slab and run on a Pulsed field gel electrophoresis (PFGE) instrument in order to isolate the cleaved fragment as a distinct DNA band on the gel. Target bands (197kb) from 5 lanes are cut out of the PFGE gel and DNA was recovered using GlAquick Gel Extraction kit (column), eluted with 15 ul elution buffer and tested the concentration on a Qubit instrument. The resulting sample contained ~0.426 ng/ul target DNA. A sequencing library was prepared using Truseq kit for library prep and the library was sequenced in a 150×2 miseq run as one of many samples in the lane. Sequencing resulted in 265386×2 reads and ~91 MGbx2 data in total, demonstrating the extremely deep coverage achievable for such a target region.

Figure 4A:
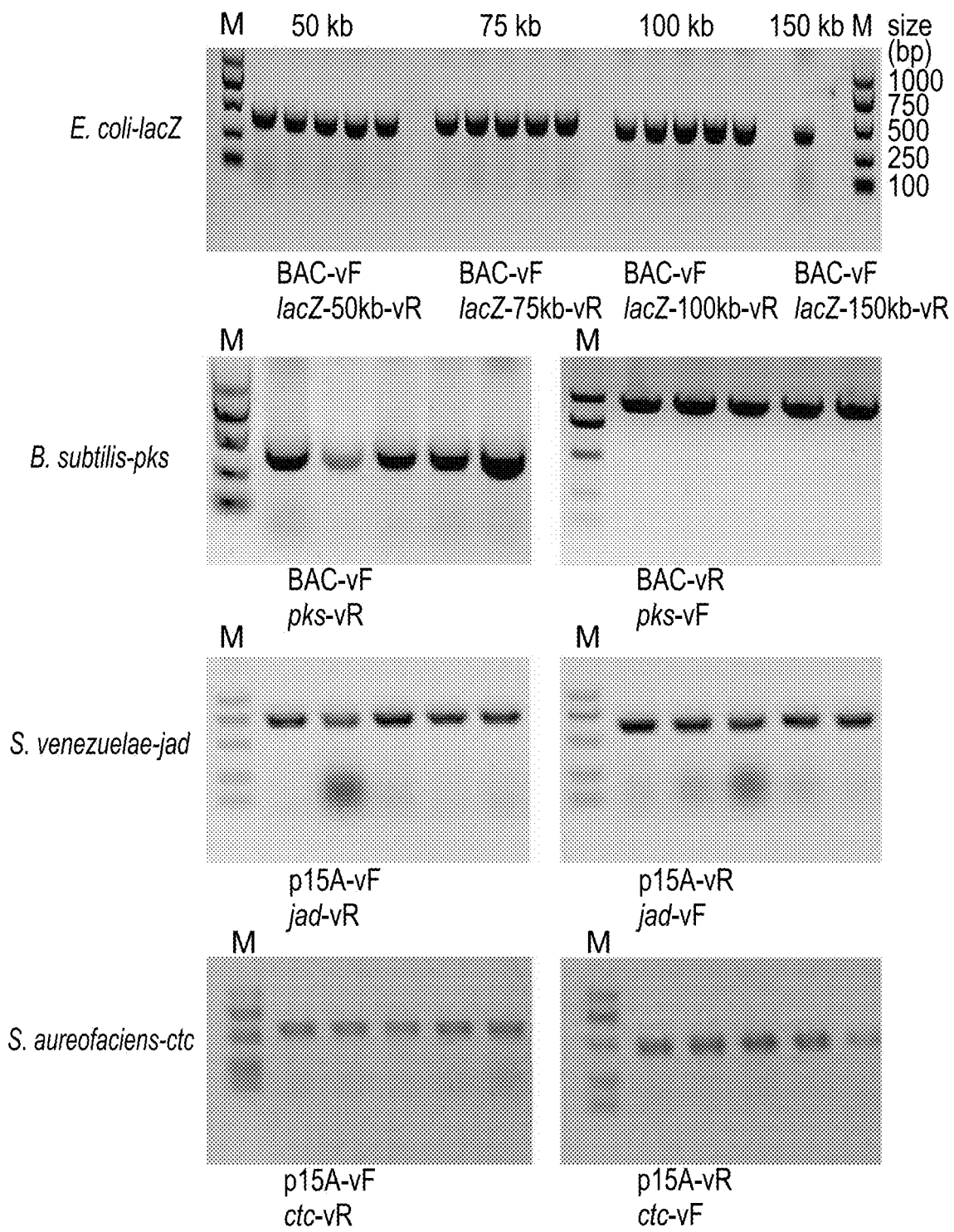
Figure 4B:
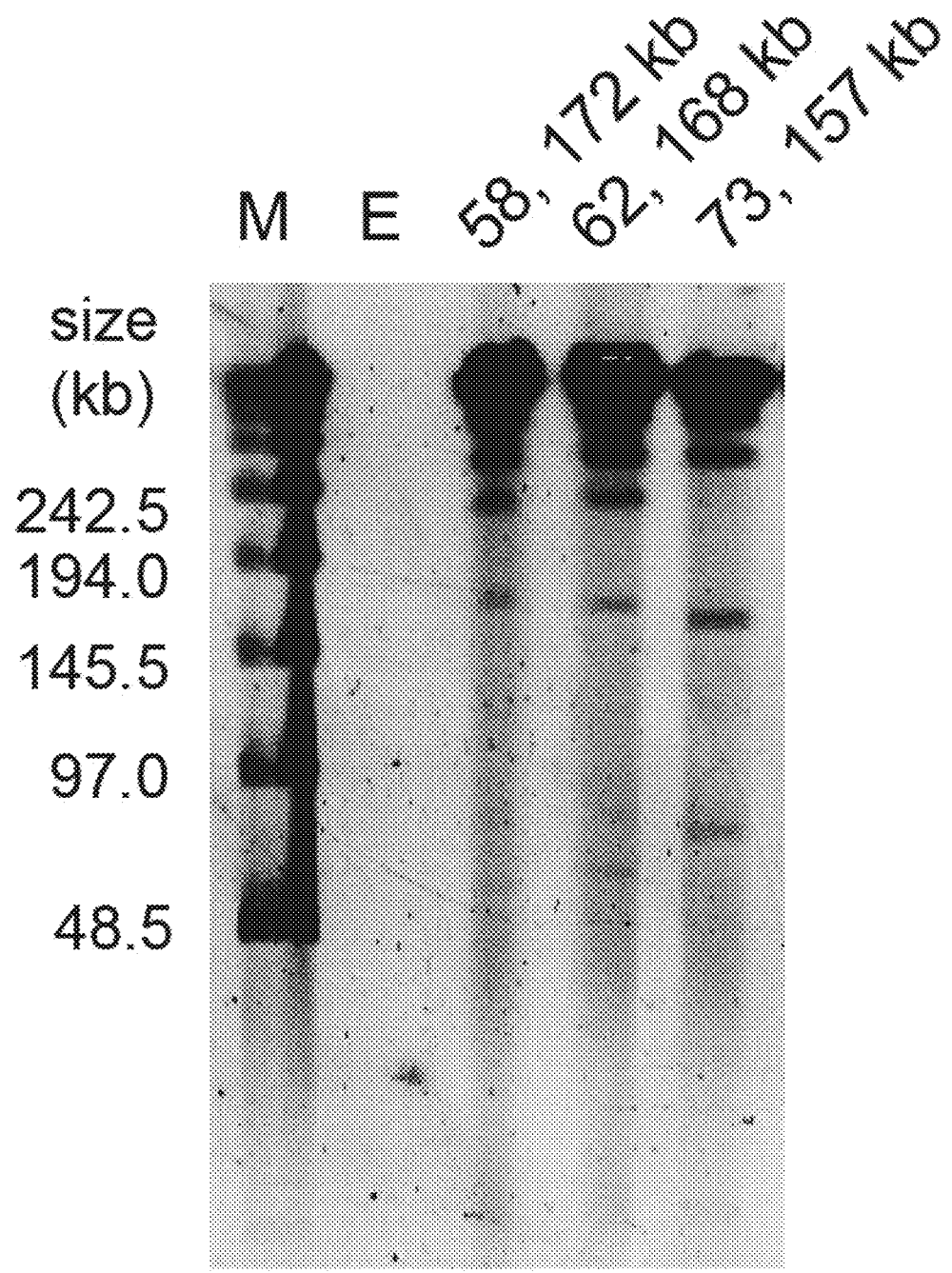

FIGS. 4A-B show in-gel Cas9 digestion of microbial genomes and validation of positive clones. FIG. 4A—shows PCR validation of positive clones carrying target inserts cloned from *E. coli, B. subtilis, S. venezuelae,* and *S. aureofaciens*, respectively (primers for validation SEQ ID NOs: 25-38). For the blue colonies with target inserts cloned from *E. coli*, PCR was performed at one of the two junction sites opposite to the *lacZ* gene, whereas for those from the others, both junction sites were validated. Names of the PCR primers used are listed below the panels. The same DNA marker was used in all panels. M, marker. FIG. 4B shows the in-gel Cas9 digested *S. cerevisiae* chromosome I (of ~230 kb) analyzed by PFGE to assess the cleavage efficiency and off-target effects. One RNA-guided Cas9 cut divides the chromosome into 2 fragments (of 58 plus 172 kb, 62 plus 168 kb, and 73 plus 157 kb, respectively) in each experiment. The expected fragment lengths are indicated above the loading wells. E, empty lane.

DESCRIPTION OF SPECIFIC EMBODIMENTS OF THE INVENTION

The present invention, in some embodiments thereof, relates to methods and kits for fragmenting DNA which can be further employed in DNA sequencing, imaging, amplification and cloning.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Whilst reducing the present invention to practice, the present inventors have devised a method for physical extraction of large genomic regions of interest for genetic analysis using an auxiliary unit-directed nuclease such as that of the bacterial CRISPR system. The genomic region of interest is separated from the genome by specifically targeting the nuclease (e.g., Cas9) to cleave a double-strand DNA at the two extremities of the region of interest. Alternatively, fragmentation may be induced by two single strand nicks in close proximity but in parallel strands. The targeting of the endonuclease is achieved by an auxiliary subunit which is not native to the nuclease, e.g., guide RNA that carries a long recognition sequence e.g., sequence of up to 20 nt that hybridize to the genome allowing highly specific targeting. Cleavage is effected in a semi-solid medium (e.g., gel), which protects genomic DNA from shearing. Gel electrophoresis is used to physically separate the genomic fragment from the rest of the genome. Pulsed field gel electrophoresis (PFGE) allows the separation of DNA up to several Mbp in length (such as intact Pombe yeast chromosomes) but will not separate the remaining genomic DNA given the large size of chromosomes (e.g., human chromosomes). The desired DNA may be excised from the gel and used for further genetic and epigenetic analysis such as sequencing or optical mapping in nanochannels. Thus the present teachings provide for targeted genomics scheme that allows addressing specific genomic regions.

By using auxiliary domain-directed nuclease in vitro, this invention can digest and isolate specific DNA fragments of up to mega bases in lengths from genome. Combining with sequencing techniques such as Sanger sequencing, next-generation sequencing, single molecule real time sequencing, nanopore sequencing and optical mapping, this invention may realize the goals of filling the gap of whole genomes of many species, fast-diagnosis of mutation-related genetic diseases and accurate detection of DNA epigenetic traits. Whatever sequencing method it is applied to, this invention would enhance its accuracy and reduce the temporal and economical costs.

Thus, according to an aspect of the invention there is provided a method of fragmenting DNA, the method comprising, incubating a semi-solid biological sample which comprises the DNA with an auxiliary domain-directed nuclease having a binding affinity and selectivity to pre-defined sites in the DNA so as to yield a DNA fragment-of-interest, to thereby fragment the DNA.

As used herein the term "fragmenting", which is interchangeably referred to as "cleaving", "digesting" or "restricting" refers to an enzymatic reaction that selectively breaks the phosphodiester bonds between two adjacent nucleotides in both strands of a double-stranded DNA molecule, thereby resulting in a double-stranded break in the DNA molecule. To generate at least one fragment, at least two cleavage events directed at different pre-defined sites in the DNA molecule must take place.

Cleavage may be a result of nicking at complementary sites of, or adjacently located on the DNA.

The term "nicking," as used herein, refers to a reaction that breaks the phosphodiester bond between two nucleotides in one strand of a double-stranded DNA molecule to produce a 3' hydroxyl group and a 5' phosphate group.

As used herein "DNA" refers to a double stranded polymer which comprises deoxyribonucleic acid nucleotides. The DNA molecule also referred to herein as a "polynucleotide" comprises at least one sequence of interest. According to some embodiments of the invention, the DNA may be of any length, e.g., greater than about 10 Kb bases, greater than about 50 Kb bases, greater than 100 Kb bases, up to complete chromosomes e.g., bacterial, yeast, plant or human. The DNA may comprise naturally occurring nucleotides, synthetic nucleotides or a combination of both as long as Watson-Crick base pairing interactions are allowed with at least a portion of the DNA molecule. The DNA may be comprised in a chromosome or a synthetic vector e.g., a cosmid, fosmid, bac or bacteriophage.

Thus, virtually any source of DNA may be used, including but not limited to genomic DNA and complementary DNA (cDNA), plasmid DNA, mitochondrial DNA, synthetic DNA, and BAC clones, etc. Furthermore, any organism, organic material or nucleic acid-containing substance can be used as a source of DNA to be processed in accordance with the present method including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, and the like.

In certain embodiments, the genomic DNA used in the method may be derived from a mammal, wherein certain embodiments the mammal is a human.

According to a specific embodiment, the DNA is genomic DNA.

According to a specific embodiment, the DNA is chromosomal DNA.

As used herein "a biological sample" refers to an in-vitro or ex-vivo sample which comprises the DNA. The biological sample may or may not comprise various analytes in addition to DNA. It may comprise naturally occurring compositions (e.g., chromosomes) or synthetic compositions (e.g., plasmids). The biological sample may be a result of isolation from a body (e.g., human body) and as such comprise cells or cell-free DNA. Thus, contemplated are bodily fluids such as whole blood, serum, plasma, cerebrospinal fluid, urine, lymph fluids, and various external secretions of the respiratory, intestinal and genitourinary tracts, tears, saliva, milk as well as white blood cells, malignant tissues, amniotic fluid and chorionic villi.

According to a specific embodiment, the DNA is comprised in a cell or cells.

Regardless of the source of the DNA, the sample is processed such that it is formulated in a semi-solid form.

The present inventors have realized that formulating the DNA in a semi solid environment allows protection of DNA from shearing.

According to a specific embodiment, the semi-solid biological sample is in a form of a gel.

As used herein, the term "gel" refers to a three-dimensional fibrous network containing from about 50%, or from about 80%, and up to 99.9% (by mass) liquid (e.g., water). A gel can be regarded as a material which is mostly liquid, yet behaves like a solid or semi-solid due to a three-dimensional crosslinked network within the liquid, made of natural and/or synthetic polymeric chains. According to some embodiments of the present invention, the gel is a hydrogel which may contain polymeric chains of various lengths and chemical compositions which may stem from monomers, oligomers, block-polymeric units, which are inter-connected (crosslinked) by chemical bonds (covalent, hydrogen and ionic/complex/metallic bonds).

As used herein, the phrase "gelling agent" describes a compound which may be added to a liquid, wherein upon its addition to the liquid, the resulting composition becomes a gel.

In some embodiments of the invention, the gel is a thixotropic gel.

As used herein, the terms "thixotropic" and "thixotropy" describe a property of a gel, whereby the gel becomes fluid when disturbed (e.g., agitated, for example, by stirring, by downstream flow), and returns to a semisolid state after the disturbance ceases.

In some embodiments, a gel is considered semisolid when capable of adhering to a vertical surface, without flowing downward.

In some embodiments, a gelling agent is partly soluble or partially immiscible in the liquid medium it is meant to jellify, and therefore transforms it into a colloid mixture (a suspension or emulsion) or colloidal dispersion, as this term is defined hereinbelow, upon applying stress/heat/stirring/sonication, or in some cases allowing ambient temperature to act over a certain time period (e.g., minutes). A gelling agent can form a network-like structure, giving the resulting solution the consistency of a semi-solid while still being composed substantially of the liquid.

A colloid or colloidal dispersion is a type of homogenous mixture of two separate phases: a dispersed phase and a continuous phase. In a colloid, the dispersed phase is made of droplets that are distributed evenly throughout the continuous phase. Colloidal dispersions, which appear like solutions, are also referred to as colloidal aerosols, colloidal emulsions, colloidal foams, colloidal dispersions, or hydrosols. Many familiar substances, including butter, milk, cream, aerosols (fog, smog, smoke), asphalt, inks, paints, glues, and sea foam, are essentially colloids. Hydrocolloid is a common term used in the art to describe a substance that forms a gel with water.

It is noted herein that each gelling agent has a set of characteristic gelling qualities, such as setting time, setting shrinkage, setting conditions (temperature, ionic strength, ionic type and pH), physico-mechanical properties of the final gel (such as springiness, brittleness and cohesiveness), reversibility of the sol-to-gel transition (such as thermo-reversibility) and other chemical and mechanical properties. It is also noted that a composition comprising more than one gelling agent typically possesses unique characteristic gelling qualities which differ from the characteristic gelling qualities of each of the individual gelling agents in the composition or of other compositions.

According to a specific embodiment, the gelling agent is agarose e.g., low melting agarose, having a melting temperature below 65° C.

Thus, other gels where the semi-solid matrix may be broken down in a controlled fashion in order to release its content. Such transitions may be induced by chemicals, enzymes, heat, light, radiation and other stimuli are contemplated herein.

Thus, the semi-solid biological sample which comprises the DNA is then incubated with the auxiliary domain directed nuclease having a binding affinity and selectivity to pre-defined site(s) in the DNA.

However, if the DNA is comprised in cells, the semi solid plug is first incubated in the presence of suitable proteases and detergents for lysing the cells in the semi-solid biological sample prior to fragmenting the DNA in the presence of the nuclease.

Typically, the semi-solid plug is incubated in the presence of lysis buffer, a buffer solution used for the purpose of lysing cells for use in molecular biology experiments. In this specific case maintaining the structure of the organelles is not critical, hence conditions can be harsh which do not maintain internal architecture. Most lysis buffers contain salts (e.g. Tris-HCl or EDTA) to regulate the acidity and osmolarity of the lysate, while detergents (such as Triton X-100 or SDS) are added to break up membrane structures.

As DNA is quite a stable molecule, the conditions for cell lysis may be quite extreme.

Specific conditions for cell lysis are provided in the Examples section which follows. According to a specific embodiment, the semisolid sample is washed to remove cellular components following cell-lysis.

Once the cells are lysed, the semi-solid biological sample (also referred to herein as "plug") is incubated in the presence of the auxiliary domain directed nuclease having a binding affinity and selectivity to pre-defined sites in the DNA so as to yield a DNA fragment-of-interest. The nuclease may be pre-assembled with the auxiliary domain or both can be added to the reaction solution separately.

As used herein the term "nuclease" refers to any polypeptide, or complex comprising a polypeptide, that can generate a strand break in DNA, e.g. in genomic DNA. The auxiliary domain-directed nuclease is site specific, conferred by the auxiliary subunit (used herein interchangeably with domain) e.g., oligonucleotide (oligonucleotide-directed). The auxiliary domain is typically not covalently bound to the nuclease.

It is noted that the combination of the nuclease and the auxiliary domain imparts the affinity and selectivity required to cleave at the target site. The auxiliary domain binds the DNA at the target site, which is typically adjacent a few bases (e.g., 1 or more e.g., 1-100 bases) to the nucleic acid sequence of interest and therefore does not affect its integrity.

Exemplary nucleases which may be used in accordance with the present teachings include restriction enzymes (e.g. type II restriction endonuclease), topoisomerases [e.g. DNA gyrase, eukaryotic topoisomerase II (topo II), and bacterial topoisomerase IV (topo IV)], recombinases (e.g. Cre recombinase, Hin recombinase), integrases, DNAses, endo-exonucleases (e.g. micrococcal nuclease) and homing endonucleases.

According to one embodiment, the nuclease utilized may comprise a non-specific DNA cleavage domain.

According to one embodiment of the present invention, the nuclease comprises an oligonucleotide-dependant nuclease such as Cas or a RISC.

RISC enzymes are taught in Martinez J, Tuschl T. RISC is a 5' phosphomonoester-producing RNA endonuclease. Genes Dev. 2004;18:975-980.

The terms "Cas9", "Cas9 enzyme" and "Cas9-gRNA complex" refer to a complex comprising a Cas9 protein and a guide RNA (gRNA). In the case, the auxiliary domain is the guide RNA which may be composed of two molecules, i.e., one RNA ("crRNA") which hybridizes to a target and provides sequence specificity, and one RNA, the "tracrRNA", which is capable of hybridizing to the crRNA. Alternatively, the guide RNA may be a single molecule (i.e., a sgRNA) that contains crRNA and tracrRNA sequences. A Cas9 protein may be at least 60% identical (e.g., at least 70%, at least 80%, or 90% identical, at least 95% identical or at least 98% identical or at least 99% identical) to a wild type Cas9 protein, e.g., to the Streptococcus pyogenes Cas9 protein. The Cas9 protein may have all the functions of a wild type Cas 9 protein, or only one or some of the functions, including nuclease activity.

According to one embodiment, the Cas9 or RISC is attached to a single guide RNA (sgRNA) to cleave genomic DNA in a sequence specific manner.

As used herein "a single guide RNA" or "sgRNA" refers to a chimeric RNA molecule which is composed of a clustered regularly interspersed short p_alindromic repeats (CRISPR) RNA (crRNA) and trans-encoded CRISPR RNA (tracrRNA). The crRNA defines a site-specific targeting of the Cas9 protein. The sequence is typically 19-22 nucleotides long e.g., 20 consecutive nucleotides complementary to the target and is typically located at the 5' end of the sgRNA molecule. The crRNA may have 100% complementation with the target sequence although at least 80%, 85%, 90%, and 95% global homology to the target sequence are also contemplated according to the present teachings.

The tracrRNA is 100-300 nucleotides long and provides a binding site for the nuclease e.g., Cas9 protein forming the CRISPR/Cas9 complex.

According to a specific embodiment a plurality of oligonucleotides e.g., sgRNAs are provided DNA that are complementary to different target nucleic acid sequences and the nuclease e.g., Cas9 enzyme cleaves the different target nucleic acid sequences in a site specific manner, so as to generate at least one DNA fragment of interest.

Thus, the oligonucleotide-directed nuclease of the invention comprises at least one nuclease (e.g. Cas9 or RISC) and at least one RNA binding domain (e.g. sgRNA). CRISPR/Cas proteins of the invention may comprise a nuclease domain, DNA binding domain, helicase domain, RNAse domain, protein-protein interaction domain and/or a dimerization domain.

According to one embodiment, the CRISPR/Cas protein can be a wild type CRISPR/Cas protein, a modified CRISPR/Cas protein, or a fragment of a wild type or modified CRISPR/Cas protein. Furthermore, the CRISPR/Cas protein can be modified to increase nucleic acid binding affinity and/or specificity, or to alter an enzymatic activity of the protein. For example, nuclease (i.e., Cas9) domains of the CRISPR/Cas protein can be modified.

Non-limiting examples of suitable Cas proteins which may be used in accordance with the present teachings include Cas3, Cas4, Cas5, Cas5e (or CasD), Cas6, Cas6e, Cas6f, Cas7, Cas8a1, Cas8a2, Cas8b, Cas8c, Cas9, Cas10, Casl Od, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3,Csx17, Csx14, Csx10, Csx16, CsaX, Csx3, Csz1, Csx15, Csf1, Csf2, Csf3, Csf4, and Cu1966.

According to a specific embodiment, the Cas nuclease is Cas9. Cas9 is a monomeric DNA nuclease guided to a DNA target sequence adjacent to the protospacer adjacent motif (PAM). The Cas9 protein comprises two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA.

In some embodiments, the CRISPR/Cas system comprises a wild type Cas9 protein or fragment thereof.

In other embodiments, the CRISPR/Cas system comprises a modified Cas9 protein. For example, the amino acid sequence of the Cas9 protein may be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein.

According to one embodiment, the Cas9 protein can be modified to lack at least one functional nuclease domain. According to one embodiment, the Cas9 protein can be modified to lack all nuclease activity. According to another embodiment, the CRISPR/Cas system is fused with various effector domains, such as DNA cleavage domains. The DNA cleavage domain can be obtained from any endonuclease or exonuclease. Non-limiting examples of endonucleases from which a DNA cleavage domain can be derived include, but are not limited to, restriction endonucleases and homing endonucleases (see, for example, New England Biolabs Catalog or Belfort et al. (1997) Nucleic Acids Res.). In exemplary embodiments, the cleavage domain of the CRISPR/Cas system is a FokI endonuclease domain or a modified FokI endonuclease domain.

Various methods for designing CRISPR/Cas are known in the art and may be implemented in accordance with the present teachings. Further details relating to CRISPR/Cas can be found in PCT publication no. WO 2014089290 which is incorporated herein by reference in its entirety.

According to another embodiment, the oligonucleotide-directed nuclease is a meganuclease.

As used herein, the term "meganuclease" refers to a double-stranded endonuclease having a large oligonucleotide recognition site, e.g. DNA sequences of at least 12 base pairs (bp) or from 12 bp to 40 bp. The meganuclease may also be referred to as rare-cutting or very rare-cutting endonuclease. The meganuclease of the invention may be monomeric or dimeric. The meganuclease may include any natural meganuclease such as a homing endonuclease, but may also include any artificial or man-made meganuclease endowed with high specificity, either derived from homing endonucleases of group I introns and inteins, or other proteins such as zinc finger proteins or group II intron proteins, or compounds such as nucleic acid fused with chemical compounds.

Artificial meganucleases of the invention include, but are not limited to, custom-made meganucleases which are meganucleases derived from any initial meganuclease, either natural or not, presenting a recognition and cleavage site different from the site of the initial meganuclease, i.e. the custom-made meganuclease cleaves a novel site with an efficacy at least 10 fold, at least 50 fold or at least 100 fold more than the natural meganuclease.

Custom-made meganucleases may be produced by any method known in the art, for example, by preparing a library of meganuclease variants and isolating, by selection and/or screening, the variants able to cleave the targeted DNA sequence. The diversity could be introduced in the meganuclease by any method known to one skilled in the art, for example, the diversity may be introduced by targeted mutagenesis (i.e. cassette mutagenesis, oligonucleotide directed codon mutagenesis, targeted random mutagenesis), by random mutagenesis (i.e. mutator strains, Neurospora crassa system (U.S. Pat. No. 6,232,112; WO 01/70946, error-prone PCR), by DNA shuffling, by directed mutation or a combination of these technologies (See Current Protocols in Molecular Biology, Chapter 8 "Mutagenesis in cloned DNA", Eds Ausubel et al., John Wiley and Sons). The diversity may be introduced at positions of the residues contacting the DNA target or interacting (directly or indirectly) with the DNA target, or may be introduced specifically at the positions of the interacting amino acids. In libraries generated by targeted mutagenesis, the 20 amino acids can be introduced at the chosen variable positions. According to an embodiment, the amino acids present at the variable positions are the amino acids well-known to be generally involved in protein-DNA interaction. More particularly, these amino acids are generally the hydrophilic amino acids, e.g. comprise D, E, H, K, N, Q, R, S, T, Y. Synthetic or modified amino acids may also be used.

The custom-made meganuclease may be derived from any initial meganuclease.

According to one embodiment the initial meganuclease is selected so as its natural recognition and cleavage site is the closest to the targeted DNA site. According to an embodiment, the initial meganuclease is a homing endonuclease. Homing endonucleases fall into 4 separated families on the basis of well conserved amino acids motifs, namely the LAGLIDADG family, the GIY-YIG family, the His-Cys box family, and the HNH family (Chevalier et al., 2001, N.A.R, 29, 3757-3774). According to one embodiment, the homing endonuclease is a I-Dmo I, PI-Sce I, I-SceI, PI-Pfu I, I-Cre I, I-Ppo I, or a hybrid homing endonuclease I-Dmo I/I-Cre I called E-Dre I (as taught in Chevalier et al., 2001, Nat Struct Biol, 8, 312-316).

Further details relating to meganucleases are found in U.S. Pat. No. 8,697,395 which is incorporated herein by reference.

According to another embodiment of the present invention, the nuclease comprises a chimeric nuclease.

As used herein the phrase "chimeric nuclease" refers to a synthetic chimeric polypeptide which forms a single open reading frame (ORF) and mediates DNA cleavage in a sequence specific manner.

According to a specific embodiment, the chimeric nucleases of this aspect of the present invention comprise separate domains for nucleic acid binding (e.g. DNA binding) and for nucleic acid cleavage (e.g. DNA cleavage), such that cleavage is sequence specific.

As used herein the phrase "sequence specific" refers to a distinct chromosomal location at which nucleic acid cleavage (e.g. DNA cleavage) is introduced.

As used herein the phrase "nucleic acid binding domain" refers to a native or synthetic amino acid sequence such as of a protein motif that binds to double- or single-stranded DNA or RNA in a sequence-specific manner (i.e. target site).

In order to induce efficient gene targeting, the nucleic acid (e.g. DNA) binding domain of the present invention needs to be coupled to a DNA cleavage domain (e.g. nuclease) as to permit DNA cleavage within a workable proximity of the target sequence. A workable proximity is any distance that still facilitates the sequence targeting. Optionally, the DNA binding domain overlaps the target sequence or may bind within the target sequence.

According to one embodiment, the chimeric nuclease induces a single stranded or a double stranded cleavage in the target site.

In generating chimeric nucleases any DNA or RNA binding domain that recognizes the desired target sequence (e.g. DNA binding sequence) with sufficient specificity may be employed. A variety of such DNA and RNA binding domains are known in the art.

Examples of DNA binding domains include, but are not limited to, a meganuclease binding domain, a helix-turn-helix (pfam 01381) binding domain, a leucine zipper (ZIP) binding domain, a winged helix (WH) binding domain, a winged helix turn helix domain (wHTH) binding domain, a helix-loop-helix binding domain, a transcription activator-like (TAL) binding domain, a recombinase, and a zinc finger binding domain.

In an exemplary embodiment of the present invention, the DNA binding domain is a zinc finger binding domain.

Thus, according to an embodiment of this aspect, the chimeric nuclease is a chimeric protein comprising a specific zinc finger binding domain (e.g., pfam00096) and the DNA cleavage domain, such as that of the FokI restriction enzyme (also referred to herein as the FokI cleavage domain), termed herein zinc finger nuclease (ZFN).

The zinc finger domain is 30 amino acids long and consists of a recognition helix and a 2-strand beta-sheet. The domain also contains four regularly spaced ligands for Zinc (either histidines or cysteines). The Zn ion stabilizes the 3D structure of the domain. Each finger contains one Zn ion and recognizes a specific triplet of DNA basepairs.

Zinc finger domains can be engineered to bind to a predetermined nucleotide sequence. Each individual zinc finger (e.g. Cys2/His2) contacts primarily three consecutive base pairs of DNA in a modular fashion [Pavletich et al., Science (1991) 252:809-817; Berg et al., Science (1996) 271:1081-1085]. By manipulating the number of zinc fingers and the nature of critical amino acid residues that contact DNA directly, DNA binding domains with novel specificities can be evolved and selected [see, e.g., Desjarlais et al., Proc. Natl. Acad. Sci. USA (1992) 89:7345-7349; Rebar et al., Science (1994) 263:671-673; Greisman et al., Science (1997) 275:657-661; Segal et al., Proc. Natl. Acad. Sci. USA (1999) 96:2758-2763]. Hence, a very wide range of DNA sequences can serve as specific recognition targets for zinc finger proteins. Chimeric nucleases with several different specificities based on zinc finger recognition have been previously disclosed [see for example, Huang et al., J. Protein Chem. (1996) 15:481-489; Kim et al., Biol. Chem. (1998) 379:489-495].

Various methods for designing chimeric nucleases with zinc finger binding domains are known in the art.

In one embodiment the DNA binding domain comprises at least one, at least two, at least 3, at least 4, at least 5 at least 6 zinc finger domains, binding a 3, 6, 9, 12, 15, or 18 nucleotide sequence, respectively. It will be appreciated by the skilled artisan that the longer the recognition sequence is, the higher the specificity that will be obtained.

Specific DNA binding zinc fingers can be selected by using polypeptide display libraries. The target site is used with the polypeptide display library in an affinity selection step to select variant zinc fingers that bind to the target site. Typically, constant zinc fingers and zinc fingers to be randomized are made from any suitable C2H2 zinc fingers protein, such as SP-1, SP-1C, TFIIIA, GLI, Tramtrack, YY1, or ZIF268 [see, e.g., Jacobs, EMBO J. 11:4507 (1992); Desjarlais & Berg, Proc. Natl. Acad. Sci. U.S.A. 90:2256-2260 (1993)]. The polypeptide display library encoding variants of a zinc finger protein comprising the randomized zinc finger, one or more variants of which will be selected, and, depending on the selection step, one or two constant zinc fingers, is constructed according to the methods known to those in the art. Optionally, the library contains restriction sites designed for ease of removing constant zinc fingers, and for adding in randomized zinc fingers. Zinc fingers are randomized, e.g., by using degenerate oligonucleotides, mutagenic cassettes, or error prone PCR. See, for example, U.S. Pat. Nos. 6,326,166, 6,410,248, and 6479626.

Zinc fingers can also be selected by design. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

According to another embodiment, the chimeric nuclease is a TALENs or a compact-TALENs (cTALENs).

As used herein, the term "TALENs" or "Transcription Activator-Like Effector Nucleases" refers to the artificial restriction enzymes generated by fusing the TAL effector DNA binding domain to a DNA cleavage domain. TALENs of the invention enable efficient, programmable, and specific DNA cleavage.

It will be appreciated that Transcription activator-like effectors (TALEs) can be quickly engineered to bind practically any DNA sequence. The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN. Further details relating to TALENS can be found in U.S. Pat. Nos. 8,450,471; 8,440,431; 8,440,432; and U.S. Patent Application No. 20140256798 all of which are incorporated herein by reference in their entirety.

TALEs are proteins secreted by Xanthomonas bacteria. The DNA binding domain of TALEs contains a highly conserved 33-34 amino acid sequence with the exception of the 12th and 13th amino acids. These two locations are highly variable [Repeat Variable Diresidue (RVD)] and show a strong correlation with specific nucleotide recognition. This simple relationship between amino acid sequence and DNA recognition has allowed for the engineering of specific DNA binding domains by selecting a combination of repeat segments containing the appropriate RVDs.

TALENs of the invention are typically constructed using a non-specific DNA cleavage domain, such as the non-specific DNA cleavage domain of FokI endonuclease. Thus, wild-type FokI cleavage domain may be used as well as FokI cleavage domain variants with mutations designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the DNA cleavage domain (e.g. FokI cleavage domain) and the number of bases between the two individual TALEN binding sites are parameters for achieving high levels of activity. The number of amino acid residues between the TALEN DNA binding domain and the DNA cleavage domain (e.g. FokI cleavage domain) may be modified by introduction of a spacer between the plurality of TAL effector repeat sequences and the nuclease (e.g. FokI endonuclease domain). The spacer sequence may be 12 to 30 nucleotides.

Furthermore, compact TALENs (cTALENs) may be used according to the present teachings. These cTALENs are typically designed with the partially specific I-TevI catalytic domain and are monomeric DNA-cleaving enzymes, i.e. TALENs which are half-size, single-polypeptide compact transcription activator-like effector nucleases (see Beurdeley M. et al., Nature Communications (2013) 4: 1762, which is incorporated herein by reference in its entirety).

The relationship between amino acid sequence and DNA recognition of the TALEN binding domain allows for designable proteins. In this case software programs (e.g. DNA-Works) may be used which calculate oligonucleotides suitable for assembly in a two step PCR; oligonucleotide assembly followed by whole gene amplification. Modular assembly schemes for generating engineered TALE constructs may also be used. Both methods offer a systematic approach to engineering DNA binding domains that are conceptually similar to the modular assembly method for generating zinc finger DNA recognition domains (described hereinabove).

Qualifying the nucleases (e.g. ZFN, TALENs and CRISPR/Cas) and meganucleases thus generated for specific target recognition can be effected using methods which are well known in the art.

The auxiliary domain e.g., sgRNAs used in the method may be designed so that they direct binding of the nuclease to pre-defined sites in the DNA so as to yield as least one FNA fragment of interest. In certain cases, the cleavage sites may be chosen so as to release a fragment that contains a region of unknown sequence, or a region containing a SNP, nucleotide insertion, nucleotide deletion, rearrangement, etc. Since genomic isolation methods, and the nucleotide sequences of many organisms (including many bacteria, fungi, plants and animals, e.g., mammals such as human, primates, and rodents such as mouse and rat) are known, designing such auxiliary domains e.g., guide RNAs for use in the present method should be within the skill of one of skilled in the art.

According to a specific embodiment, the DNA fragment-of-interest is 10-150 Kb in length. According to a specific embodiment, the DNA fragment-of-interest is 20-150 Kb in length. According to a specific embodiment, the DNA fragment-of-interest is 30-150 Kb in length. According to a specific embodiment, the DNA fragment-of-interest is 40-150 Kb in length. According to a specific embodiment, the DNA fragment-of-interest is 50-150 Kb in length. According to a specific embodiment, the DNA fragment-of-interest is 60-150 Kb in length. According to a specific embodiment, the DNA fragment-of-interest is 70-150 Kb in length. According to a specific embodiment, the DNA fragment-of-interest is 80-150 Kb in length. According to a specific embodiment, the DNA fragment-of-interest is 90-150 Kb in length. According to a specific embodiment, the DNA fragment-of-interest is 100-150 Kb in length. According to a specific embodiment, the DNA fragment-of-interest is 50-100 Kb in length. According to a specific embodiment, the DNA fragment-of-interest is 60-100 Kb in length. According to a specific embodiment, the DNA fragment-of-interest is 70-100 Kb in length. According to a specific embodiment, the DNA fragment-of-interest is 80-100 Kb in length. According to a specific embodiment, the DNA fragment-of-interest is 80-140 Kb in length. According to a specific embodiment, the DNA fragment-of-interest is 80-130 Kb in length.

Since the present teachings are particularly useful in generating large fragments of DNA, they can even be used in the isolation of complete gene clusters or operons from genomic DNA. These can for example include complete Polyketide synthase (pks) clusters or nonribosomal peptide synthetases. Conditions for effecting the enzymatic reaction of fragmentation once the DNA is fragmented, the fragment of interest may be useful in any of a number of molecular biology applications, examples of which are provided hereinbelow.

Thus, the DNA fragment of interest may be cloned.

Interestingly, the present inventors have found that cloning of the DNA fragment-of-interest does not necessitate the separation thereof from the DNA, although such a separation may still take place.

As used herein the term "separating" or "partitioning," refers to the separation of the DNA fragment-of-interest from the remainder of the DNA e.g., genome, to produce a product that is isolated. The term "partitioning" encompasses enriching.

Thus, in some embodiments, the fragments produced by the method may be cloned into a vector, e.g., a fosmid, bac or cosmid vector for storage and later analysis.

In some cases, the fragments may be treated with Taq polymerase to produce that contain a 3' A overhang, and then cloned by TA cloning. The fragments (whether or not they are cloned in a vector) may be genotyped, e.g., sequenced. In some cases, the fragments may be amplified prior to cloning and/or analysis, which may involve ligating adaptors onto the ends of the fragments, and amplifying the fragments using primers that hybridize to the ligated adaptors.

According to one embodiment, the cloning is effected by Gibson assembly. In such a case, following fragmenting (as described above), the semi-solid biological sample is melted (by increasing the temperature) and then subjected to enzymatic treatment which digests the gel matrix of the semi-solid biological sample. Thus, for instance, where the matrix is agarose (e.g., low melting agarose), the plug is subjected to high temperature e.g., above 45° C.

The use of Gibson assembly is particularly contemplated, taking advantage of the high sequence specificity of this reaction, without the need for size-selection and gel purification from the background DNA (e.g., genomic). An exemplary outline of this reaction is provided infra. First BAC vectors that share terminal sequence overlaps with the target DNA are prepared (see Methods further below). The digested plugs are further purified by ethanol precipitation and resuspended in buffer or nuclease-free water (see Methods). The recovered DNA and vector are mixed in a Gibson assembly mix containing T5 5'-3' exonuclease, Taq DNA ligase, and high-fidelity polymerase.

Finally, the ligation mix is transformed into *E. coli* competent cells.

As mentioned, the fragmented DNA may be further subjected to other high performance molecular biology protocols.

Some examples are provided hereinbelow.

Thus, according to one embodiment, there is provided a method of DNA sequencing, the method comprising:
(a) fragmenting a DNA, so at to obtain at least one DNA fragment-of-interest;
(b) separating the DNA fragment-of-interest from the DNA; and
(c) sequencing the DNA fragment-of-interest.

According to an alternative or additional embodiment, there is provided a method of nucleic acid amplification, the method comprising:
(a) fragmenting a DNA, so at to obtain at least one DNA fragment-of-interest;
(b) separating the DNA fragment-of-interest from the DNA; and
(c) amplifying the DNA fragment-of-interest.

According to an alternative or additional embodiment there is provided a method of in situ imaging DNA, the method comprising:
(a) fragmenting a DNA, so at to obtain at least one DNA fragment-of-interest;
(b) separating the DNA fragment-of-interest from the DNA;
(c) attaching a labeling agent to the DNA fragment-of-interest; and
(d) subjecting the DNA fragment-of-interest to an imaging method suitable for detecting said labeling agent.

In each of these methods the step of separation (partitioning) is typically done by gel electrophoresis. The use of pulsed-field gel electrophoresis negates the need for melting the semi-solid biological sample and further subjecting it to enzymatic treatment which digests the gel matrix.

Pulsed field gel electrophoresis (PFGE) is a technique used for the separation of large deoxyribonucleic acid (DNA) molecules by applying to a gel matrix an electric field that periodically changes direction. Accordingly, at least a portion of the plug (i.e., the semi-solid biological sample following fragmenting) is located in the well of the PFGE and subjected to the procedure.

The present teachings may thus be employed to isolate promoters, terminators, exons, introns, entire genes, homologous genes, sets of gene sequences that are linked by function (e.g., operons and clusters, as mentioned above), expression or sequence, regions containing insertion, deletion or translocation breakpoints or SNP-containing regions, epigenetic modifications (e.g., for example methylation). Alternatively, the method could be used to reduce the sequence complexity of a genome prior to analysis, or to enrich for genomic regions of interest.

In certain embodiments the method may be used to produce fragments of interest (i.e., one or more regions of a genome), where the resultant sample is at least 50% free, e.g., at least 80% free, at least 90% free, at least 95% free, at least 99% free of the other parts of the genome. In particular embodiments, the products of the method may be amplified before analysis. In other embodiments, the products of the method may be analyzed in an unmodified form, i.e., without amplification.

As noted above, the method may be employed to isolate a region of interest from a genome. The isolated region may be analyzed by any analysis method including, but not limited to, DNA sequencing (using Sanger, pyrosequencing or the sequencing systems of Roche/454, Helicos, Illumina/Solexa, ABI (SOLiD), PacBio and Oxford nanopore), a polymerase chain reaction assay, a hybridization assay, a hybridization assay employing a probe complementary to a mutation, a microarray assay, a bead array assay, a primer extension assay, an enzyme mismatch cleavage assay, a branched hybridization assay, a NASBA assay, a molecular beacon assay, a cycling probe assay, a ligase chain reaction assay, an invasive cleavage structure assay, an ARMS assay, or a sandwich hybridization assay, for example. Some products (e.g., single-stranded products) produced by the method may be sequenced, and analyzed for the presence of SNPs or other differences relative to a reference sequence. As would be clear to one skilled in the art, the proposed method may be useful in several fields of genetic analysis, by allowing the artisans to focus their analysis on a genomic region of interest.

As mentioned, the present teachings may also be used in in-situ imaging whereby following separation of the DNA fragment-of-interest, a labeling agent is attached to the fragment and subjected to an imaging method suitable for detecting the labeling agent. Thus, embodiments of the invention relate to methods of labeling a DNA fragment of interest and imaging the labeled DNA molecule at the single molecule level, while maintaining high sensitivity. Such methods are described in WO2014191981 and are particularly useful in detecting epigenetic modifications.

As used herein a "labeling agent" refers to a detectable moiety or a probe. Exemplary labeling agents which are suitable for use in the context of these embodiments include, but are not limited to, a fluorescent agent, a radioactive agent, a magnetic agent, a chromophore, a bioluminescent agent, a chemiluminescent agent, a phosphorescent agent and a heavy metal cluster, as well as any other known detectable agents.

In some embodiments, the labeling agent is an agent that is detectable by spectrophotometric measurements, and/or which can be utilized to produce optical imaging. Such agents include, for example, chromophores, fluorescent agents, phosphorescent agents, and heavy metal clusters.

As used herein, the term "chromophore" refers to a chemical moiety that, when attached to another molecule, renders the latter colored and thus visible when various spectrophotometric measurements are applied.

The phrase "fluorescent agent" refers to a compound that emits light at a specific wavelength during exposure to radiation from an external source.

The phrase "phosphorescent agent" refers to a compound emitting light without appreciable heat or external excitation as by slow oxidation of phosphorous.

A heavy metal cluster can be for example a cluster of gold atoms used, for example, for labeling in electron microscopy techniques (e.g., AFM).

The term "bioluminescent agent" describes a substance which emits light by a biochemical process.

The term "chemiluminescent agent" describes a substance which emits light as the result of a chemical reaction.

According to some embodiments of the invention, the labeling agent is a fluorescent labeling agent.

A fluorescent agent can be a protein, quantum dots or small molecules. Common dye families include, but are not limited to Xanthene derivatives: fluorescein, rhodamine, Oregon green, eosin, Texas red etc.; Cyanine derivatives: cyanine, indocarbocyanine, oxacarbocyanine, thiacarbocyanine and merocyanine; Naphthalene derivatives (dansyl and prodan derivatives); Coumarin derivatives; oxadiazole derivatives: pyridyloxazole, nitrobenzoxadiazole and benzoxadiazole; Pyrene derivatives: cascade blue etc.; BODIPY (Invitrogen); Oxazine derivatives: Nile red, Nile blue, cresyl violet, oxazine 170 etc.; Acridine derivatives: proflavin, acridine orange, acridine yellow etc.; Arylmethine derivatives: auramine, crystal violet, malachite green; CF dye (Biotium); Alexa Fluor (Invitrogen); Atto and Tracy (Sigma Aldrich); FluoProbes™ (Interchim); Tetrapyrrole derivatives: porphin, phtalocyanine, bilirubin; cascade yellow; azure B™; acridine orange; DAPI; Hoechst 33258; Lucifer Yellow™; piroxicam; quinine and anthraqinone; squarylium; oligophenylenes; and the like.

Other fluorophores include: Hydroxycoumarin; Aminocoumarin; Methoxycoumarin; Cascade Blue™; Pacific Blue; Pacific Orang™e; Lucifer Yellow™; NBD; R-Phycoerythrin (PE); PE-Cy5™ conjugates; PE-Cy7 conjugates; Red 613™; PerCP™; TruRed™; FluorX™; Fluorescein; BODIPY-FL™; TRITC™™; X-Rhodamine; Lissamine Rhodamine B™; Texas Red™; Aliaphycocyanin; APC-Cy7™ conjugates.

Alexa™ Fluor dyes (Molecular Probes) include: Alexa™ Fluor 350, Alexa™ Fluor 405, Alexa™ Fluor 430, Alexa™ Fluor 488, Alexa™ Fluor 500, Alexa™ Fluor 514, Alexa™ Fluor 532, Alexa™ Fluor 546, Alexa™ Fluor 555, Alexa™ Fluor 568, Alexa™ Fluor 594, Alexa™ Fluor 610, Alexa™ Fluor 633, Alexa™ Fluor 647, Alexa™ Fluor 660, Alexa™ Fluor 680, Alexa™ Fluor 700, Alexa™ Fluor 750, and Alexa™ Fluor 790.

Cy™ Dyes (GE Healthcare) include Cy2, Cy3, Cy3B, Cy3.5, Cy5, Cy5.5 and Cy7.

Nucleic acid probes include Hoechst 33342, DAPI, Hoechst 33258, SYTOX™ Blue, ChromomycinA3, Mithramycin, YOYO-1™, Ethidium Bromide, Acridine Orange, SYTOX™ Green, TOTO-1™, TO-PRO-1, TO-PRO: Cyanine Monomer, Thiazole Orange, Propidium Iodide (PI), LDS 751, 7-AAD, SYTOX Orange, TOTO-3, TO-PRO-3, and DRAQ5.

In some embodiments, each of the labeling agents (e.g., fluophores) is attached to the DNA molecule by means of click chemistry although other methods of attaching the labeling agent are also contemplated and are well known to those of skills in the art.

Compositions of the present invention may be packaged in kits which may be accompanied by appropriate instructions for use.

Thus, according to some embodiments of the invention there is provided a kit for DNA fragmentation, the kit comprising:
(i) a first container comprising an auxiliary domain-directed nuclease;
(ii) a second container comprising low melting gel matrix; and optionally
(iii) a third container comprising a cell lysis buffer.

According to a specific embodiment, the auxiliary domain e.g., gRNA is not part of the kit since this is sequence specific.

According to an optional embodiment, the kit comprises a further container comprising an exonuclease for Gibson assembly.

According to an optional embodiment, the kit comprises a further container comprising a polymerase.

According to an optional embodiment, the kit comprises a further container comprising a labeling agent.

It is expected that during the life of a patent maturing from this application many relevant oligonucleotide-directed nucleases will be developed and the scope of the term "oligonucleotide-directed nuclease" is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, N.Y. (1988); Watson et al., "Recombinant DNA", Scientific American Books, N.Y.; Birren et al. (eds) "Genome Analysis: A Laboratory Manual Series", Vols. 1-4, Cold Spring Harbor Laboratory Press, N.Y. (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience Materials and Methods Cas9 preparation—The pET-based expression vector (SI) encoding *S. pyogenes* Cas9 followed by a His$_6$-tag was provided by Prof. Then Xie (Tsinghua, Beijing). The protein was purified mainly as previously described in Jinek et al., Science 17 August 2012: Vol. 337 no. 6096 pp. 816-821, except that (1) no glycerol was added in the Ni-NTA column elution buffer, (2) His-tag wasn't cleaved from the protein, (3) the protein was purified only by chromatography on Mono S column (GE Healthcare) (4) since the protein fraction was pure enough, the step of gel filtration was omitted. Finally the protein was concentrated to ~0.1 mg/ml and stored in 20 mM HEPES, 150 mM KCl, 1 mM DTT. 50% glycerol, pH 7.5 at ~20° C. T7 RNA polymerase protein expression plasmid was provided by Prof. Yan Nieng (Tsinghua, Beijing) and purified as previously described [Zawadzki, V. & Gross, H. J. Rapid and Simple Purification of T7 Rna-Polymerase. *Nucleic Acids Res* 19, 1948-1948, (1991)].

The in-vitro transcription (IVT) was performed in a buffer containing 100 mM Tris-HCl, pH8.0, 10 mM MgCl$_2$, 30 mM DTT, 2 mM Spermidine, 2.5 mM each rNTP, 100 ng/ul PCR production, 10% DMSO, 50 ug/ml T7 RNA polymerase and incubated at 37° C. for 2 hrs.

sgRNA preparation—The sgRNA IVT templates were prepared by overlapping PCR of 3 primers: a primer (X-sgRNA-P) containing the T7 promoter and target sequence, and 2 others (sgRNA-F and sgRNA-R) containing crRNA-tracrRNA chimera sequence of the sgRNA. All the primers used in this study are listed in Table 1. The PCR product was purified by phenol (pH>7.8)/chloroform extraction and isopropanol precipitation, followed by resuspension in RNase-free water. The IVT was performed at 37° C. for 2 h in 100 mM Tris-HCl, pH 8.0, 10 mM MgCl$_2$, 30 mM DTT, 2 mM Spermidine, 2.5 mM (each) rNTP, 10% DMSO, 100 ng/µl PCR product, and 50 µg/ml T7 RNA polymerase. After incubation, the IVT product was purified by phenol (pH<5.2)/chloroform extraction and isopropanol precipitation. Finally, the sgRNA was resuspended in RNase-free water at a concentration of 300 ng/µl and stored at −80° C.

Cell Lysis—*E. coli* or *B. subtilis* cells were embedded in agarose gel plugs at 5×10$^8$ cells/ml (~2.5 ug/ml DNA). These plugs were treated by lysozyme, proteinase K (the final concentration of lysozyme was 0.25 mg/ml, and proteinase K was 0.1 mg/ml), and washed by buffer successively according to instructions of the CHEF Bacterial Genomic DNA Plug Kit (Bio-Rad). In the second wash, 1 mM of PMSF was added to inactivate the residual proteinase K and 0.1× wash buffer was used for the last wash. The *Streptomyces* mycelia were harvested and used for making gel plugs, as described by Kieser et al.[26] The well-washed plugs can be stored in 1× wash buffer at 4° C. for 2 months, and another round of wash should be performed using 0.1× wash buffer immediately before Cas9 digestion.

For the cleavage reaction, 2 plugs (200 ul)were first equilibrated at room temperature for 30 min in 1 ml RNase-free cleavage buffer containing 20 mM HEPES, 150 mM KCl, 10 mM MgCl$_2$, 0.5 mM DTT, and 0.1 mM EDTA at pH 7.5, and then transferred into a new batch of cleavage buffer (at least 240 ul) that contains Cas9 protein (0.1 mg/ml) and the corresponding sgRNA pair (each at 30 ng/µl) and incubated at 37° C. for 2 h. After the reaction, the plugs were washed with 0.1× wash buffer, and ⅓ of a gel plug was cut out and used to assess the cleavage efficiency by PFGE. The PFGE was performed with 1% agarose gel in 0.5×TBE using the CHEF Mapper XA system (Bio-Rad) set to auto algorithm program with 5 kb to 250 kb parameters (6V/cm, 0.22 s to 21.79 s, 15 h 16 min,120°) and with circulation at 14° C. After PFGE, the gel was stained with SYBR Gold (Life Technologies) and the DNA bands were visualized using a ChemiDoc XRS+ Imaging System (Bio-Rad). The rest of the plugs (5/3, from a total of 2 starting plugs) were melted and digested by agarose according to instructions of the GELase Agarose Gel-Digesting Preparation Kit (Epicentre). The digested DNA was precipitated by ethanol and resuspended gently in 20 µl DNase-free water with wide-bore tips. The obtained DNA can be stored at 4° C. for several days, although immediate ligation is preferred.

Gibson Assembly—The vectors were prepared by PCR amplification using pCC1BAC (Epicentre) or p15A vectors as templates, followed by DpnI (NEB) treatment[27]. Each PCR primer consisted of a ~20 nt sequence that annealed to the vector template and a ~30 nt overhang that overlapped with one end of the target DNA. The Gibson assembly mix was prepared as described in the one-step isothermal DNA assembly protocol [9]. A volume of 1 µl vector (~50 ng) and 4 µl of previously prepared target DNA that appeared viscous were added to 15 µl of Gibson assembly mix by gentle pipetting and incubated at 50° C. for 1 h. After ligation, 2 µl of the mix was transformed into 50 µl TransforMax EPI300 (Epicentre) electrocompetent *E. coli* cells in a 1-mm cuvette (BTX) at 1,300 V using the ECM 399 Electroporation system (BTX). The cells were recovered at 37° C. for 2 h in 1 ml LB medium without antibiotics and then plated on LB medium containing 12.5 µg/ml chloramphenicol, IPTG, and X-gal. After incubation at 37° C. for 12 h, the blue colonies were selected for PCR at one of the two junction sites opposite to the *lacZ* gene (with one primer on pCC1BAC (BAC-vF) and the other on the insert (*lacZ*-X kb-vR)). The positive clones were grown in 5 ml LB medium overnight at 37° C. containing 12.5 µg/ml chloramphenicol and 3 µl CopyControl BAC Autoinduction Solution (Epicentre). Plasmids were extracted from these cells using the QIAprep Miniprep Kit using the QIAcube system (Qiagen) according to the manufacturer's instructions. The purified plasmids were linearized by λ-Terminase (Epicentre) and analyzed by PFGE as described above. For cloning the pks gene cluster from *B. subtilis*, no IPTG or X-gal was added in the LB medium and all colonies were PCR-validated at both junction sites (FIG. 1). The jad gene cluster from *S. venezuelae* and ctc gene cluster from *S. aureofaciens* were cloned into p15A vector using a similar method, except that the colonies were grown on LB medium with 50 µg/ml ampicillin and the plasmids were linearized by XbaI.

TABLE 1

PCR primers sgRNA template primers

| | |
|---|---|
| sgRNA-F | 5'-GTTTTAGAGCTAGAAATAGCAAGTTAAAATAAGGCTAGTC-3'/(SEQ ID NO: 1) |
| sgRNA-R | 5'-AAAAGCACCGACTCGGTGCCACTTTTTCAAGTTGATAACGGACTAGCCTTATTTTAACT-3'/(SEQ ID NO: 2) |

TABLE 1-continued

PCR primers

| | |
|---|---|
| lacZ-sgR1-P | 5'-TAATACGACTCACTATAggtgcggatatctcggtagtGTTTTAGAGCTAGAAATAGCAA-3'/(SEQ ID NO: 3) |
| lacZ-sgR2-P | 5'-TAATACGACTCACTATAggtaggatcataaagtcctcGTTTTAGAGCTAGAAATAGCAA-3'/(SEQ ID NO: 4) |
| lacZ-sgR3-P | 5'-TAATACGACTCACTATAgaatctgtcgccgaagtaaaGTTTTAGAGCTAGAAATAGCA-3'/(SEQ ID NO: 5) |
| lacZ-sgR4-P | 5'-TAATACGACTCACTATAgctgtcggggtgaatttgctGTTTTAGAGCTAGAAATA-3'/(SEQ ID NO: 6) |
| lacZ-sgR5-P | 5'-TAATACGACTCACTATAgctgtttacctataatagtcGTTTTAGAGCTAGAAATA-3' (SEQ ID NO: 39) |
| lacZ-sgR6-P | 5'-TAATACGACTCACTATAgtaaatctggggatggcgctGTTTTAGAGCTAGAAATA-3'/(SEQ ID NO: 7) |
| pks-sgR1-P | 5'-TAATACGACTCACTATAgtaaacagctgcaatcccatGTTTTAGAGCTAGAAATAGCA-3'/(SEQ ID NO: 8) |
| pks-sgR2-P | 5'-TAATACGACTCACTATAgcctatgagattcctttattGTTTTAGAGCTAGAAATAGCA-3'/(SEQ ID NO: 9) |
| jad-sgR1-P | 5'-TAATACGACTCACTATAggcgaagtccttgcccatgatGTTTTAGAGCTAGAAATAGCAA-3'/(SEQ ID NO: 10) |
| jad-sgR2-P | 5'-TAATACGACTCACTATAggacgacgaggatccgacctgaGTTTTAGAGCTAGAAATAGCAA-3'/(SEQ ID NO: 11) |
| ctc-sgR1-P | 5'-TAATACGACTCACTATAggacccaccggaggacttcgcaGTTTTAGAGCTAGAAATAGCA-3'/(SEQ ID NO: 12) |
| ctc-sgR2-P | 5'-TAATACGACTCACTATAggtctccaccgtctaccgcgacGTTTTAGAGCTAGAAATA-3'/(SEQ ID NO: 13) |
| 197 kb-seq-sgR1-P | 5'-TAATACGACTCACTATAgggcaaaaatgccgaagatgGTTTTAGAGCTAGAAATAGCAA-3/(SEQ ID NO: 40) |
| 197 kb-seq-sgR2-P | 5'-TAATACGACTCACTATAggatatcgccggagtcctcgGTTTTAGAGCTAGAAATAGCAA-3'/(SEQ ID NO: 41) |

Vector amplification primers

| | |
|---|---|
| lacZ-BAC-F | 5'-tgagctgtcttcggtatcgtcgtatcccactttattatcacTTATTCAGGCGTAGCAAC-3'/(SEQ ID NO: 14) |
| lacZ-50 kb-BAC-R | 5'-gacatgccaaaagagtggacaacgacccgagGCGGCCGCATCGAATATAA-3'/(SEQ ID NO: 15) |
| lacZ-75 kb-BAC-R | 5'-gccgtttcaaatctaacactcgtaatttacccttGCGGCCGCATCGAATATAA-3'/(SEQ ID NO: 16) |
| lacZ-100 kb-BAC-R | 5'-agcaacgactgatagtagtatcttccccagcGCGGCCGCATCGAATATAA-3'/(SEQ ID NO: 17) |
| lacZ-150 kb-BAC-R | 5'-ttttgctgccaccagatttgcgccgcccgacGCGGCCGCATCGAATATAA-3'/(SEQ ID NO: 18) |
| pks-BAC-F | 5'-gttttcttggtgaatatgaagctcacctaatttattatcacTTATTCAGGCGTAGCAAC-3'/(SEQ ID NO: 19) |
| pks-BAC-R | 5'-taccgcggagcctcagcgaccgcagcccatgGCGGCCGCATCGAATATAA-3'/(SEQ ID NO: 20) |

TABLE 1-continued

PCR primers

| | |
|---|---|
| jad-p15A-F | 5'-agtgccacaagcgtctaggggagctccacatGGTGAAGATCCTTTTTGATAATCTCATG-3'/(SEQ ID NO: 21) |
| jad-p15A-R | 5'-cggcggaggtgccgtggaagccgggccgtcaTAGATCCTTTTGGTTCATGTGCAGCTC-3'/(SEQ ID NO: 22) |
| ctc-p15A-F | 5'-gcctctggccggccggggaaagcagccatgcGGTGAAGATCCTTTTTGATAATCTCATG 3'/(SEQ ID NO: 23) |
| ctc-p15A-R | 5'-gcaggtgggtgagggtgtcggtcatcccgtcTAGATCCTTTTGGTTCATGTGCAGCTC-3'/(SEQ ID NO: 24) |

Validation primers

| | |
|---|---|
| BAC-vF | 5'-agtccgagctcatcgctaat-3'/(SEQ ID NO: 25) |
| BAC-vR | 5'-ggatagtgttcacccttgttaca-3'/(SEQ ID NO: 26) |
| lacZ-50 kb-vR | 5'-gcattttgattcacagcagtca-3'/(SEQ ID NO: 27) |
| lacZ-75 kb-vR | 5'-gacgataaccttagagggatgat-3'/(SEQ ID NO: 28) |
| lacZ-100 kb-vR | 5'-cgagctttaatgcctctgct-3'/(SEQ ID NO: 29) |
| lacZ-150 kb-vR | 5'-attcctgtgccttaatgacaat-3'/(SEQ ID NO: 30) |
| pks-vF | 5'-ccatacaatcatcgtatcgggt-3'/(SEQ ID NO: 31) |
| pks-vR | 5'-ccctccatccctcgttctaa-3'/(SEQ ID NO: 32) |
| p15A-vF | 5'-gagtccaacccggtaagacacgac-3'/(SEQ ID NO: 33) |
| p15A-vR | 5'-gagcgtccctcccggacc-3'/(SEQ ID NO: 34) |
| jad-VF | 5'-acggacgagatccacacgg-3'/(SEQ ID NO: 35) |
| jad-VR | 5'-tcgccctggccctggacag-3'/(SEQ ID NO: 36) |
| ctc-VF | 5'-gaccgagagcgcggccacc-3'/(SEQ ID NO: 37) |
| ctc-VR | 5'-tggcgacaggcgcgagtga-3'/(SEQ ID NO: 38) |

For the yeast assays (shown in FIG. 4B):

yeast-sgR1-P:
(SEQ ID NO: 42)
5'-
TAATACGACTCACTATAgggtctggaatggtacagttGTTTTAGAGCTAG
AAATAGCAA yeast-sgR2-P:
(SEQ ID NO: 43)
5'-
TAATACGACTCACTATAgaaagccaataaaagtaagaGTTTTAGAGCTAG
AAATAGCAA yeast-sgR3-P:
(SEQ ID NO: 44)
5'-
TAATACGACTCACTATAgaccaagctaaacaattattGTTTTAGAGCTAG
AAATAGCAA sgR1, 2, and 3 correspond to the 3 lanes from left to right in FIG. 4B, respectively.

Results

In the present cloning method by the CRISPR-Cas9-Assisted Targeting of CHromosome segments (CATCH) (FIG. 1), bacterial chromosomes are digested by RNA-guided Cas9 at designated target sites in agarose gel after cell lysis. The cloning vectors are designed so that they share terminal sequence overlaps (30 bp) with the target DNA at both ends, and are ligated to the target DNA through sequence complementarity in a Gibson assembly mix[7]. The recombinant plasmids are then electrotransformed into a cloning host. The procedure takes ~8 h of bench time over 1-2 days to accomplish using standard equipment and at low costs, which drastically simplifies and accelerates efforts to clone large bacterial genomic sequences.

Specifically, to test the nuclease activity of Cas9 in agarose gel and its effectiveness in isolating long DNA sequences, 5 single-guide RNA (sgRNA) pairs were designed to target fragments of different lengths (50, 75, 100, 150, and 200 kb, respectively; see Methods) in the *Escherichia coli* genome, all containing a *lacZ* gene (FIG. 2A). After being embedded in low melting temperature agarose gel plugs, bacterial cells were treated by lysozyme and proteinase K, and washed by buffer successively to remove cellular components, leaving behind the genomic DNA. The intact chromosomes were protected by the agarose matrix, allowing for further manipulations with minimal mechanical shearing. The plugs were soaked in a reaction buffer containing pre-assembled Cas9 with the corresponding sgRNA pair and incubated at 37° C. for 2 h to allow for sufficient enzyme diffusion and digestion of genomic DNA in agarose gel. After digestion, a third from the plug was cut out for pulsed-field gel electrophoresis (PFGE) to assess the cleavage efficiency (FIG. 2B). A clear band at the expected length was observed in each of the 5 lanes, while the control lanes showed either no band or heavy smear, suggesting sufficient cleavage specificity and efficiency of the RNA-guided Cas9 in agarose gel.

Having successfully cleaved the long genomic sequences of interest from bacterial chromosomes, the target DNA was ligated into BAC vectors in a Gibson assembly mix[7], taking advantage of the high sequence specificity of Gibson assembly, without the need for size-selection on PFGE and gel purification from the background genomic DNA. First BAC vectors that shared 30 bp terminal sequence overlaps with the target DNA were prepared (see Methods). The remaining of the Cas9-digested plugs (5/3, from a total of 2 starting plugs) were pooled, melted, and digested by agarase, after which the DNA content was purified by ethanol precipitation and resuspension in nuclease-free water (see Methods). The recovered DNA and vector were mixed in a Gibson assembly mix containing T5 5'-3' exonuclease, Taq DNA ligase, and high-fidelity polymerase. Finally, the ligation mix was electrotransformed into *E. coli* competent cells. Depending on the length of the target DNA to be cloned, 50-100 colonies were obtained on selective LB plates containing chloramphenicol, IPTG, and X-gal, among which 20-65% appeared blue (FIG. 2C). All blue clones were selected and validated by PCR at one of the two junction sites opposite to the *lacZ* gene (see Methods, above, FIG. 4A). The cloned BAC plasmids were purified, linearized, and analyzed by PFGE (FIG. 2D). All of the blue colonies appeared to be positive clones with correct insert sizes ranging from 50-150 kb.

Encouraged by the successful targeted isolation and cloning of genomic sequences from *E. coli* at variable lengths, the cloning of large gene clusters from other bacterial genomes was attempted. Here, the method was tested on cloning the 78 kb bacillaene-producing psk gene cluster (the largest gene cluster in Bacillus subtilis)[16] into BAC vector. Using the same method mentioned above, a total of 12 positive colonies was obtained in 3 trials with a ~12% positive rate (FIGS. 4A and 2E). Additionally, the 36 kb jadomycin-producing jad gene cluster from *Streptomyces venezuelae*[17] and the 32 kb chlortetracycline-producing ctc gene cluster from *Streptomyces aureofaciens*[18] were cloned into p15A vector. Overall, about 60 positive colonies were obtained in each experiment, with positive rates ~90% (FIG. 4A and 2F), denoting the versatility of CATCH on cloning various bacterial genomic sequences into different cloning vectors. FIG. 4B shows the in-gel Cas9 digested *S. cerevisiae* chromosome I (of ~230 kb), analyzed by PFGE to assess the cleavage efficiency and off-target effects. One RNA-guided Cas9 cut divides the chromosome into 2 fragments (of 58 plus 172 kb, 62 plus kb, and 73 plus 157 kb, respectively) in each experiment. The expected fragment lengths are indicated above the loading wells. E, empty lane.

FIG. 3 depicts the results for targeted sequencing in *E. coli*. A 197 kb genomic region has been selected and cleaved "in-gel" as described above. The gel plug containing the fragmented genomic material is placed in the well of an agarose slab and run on a Pulsed field gel electrophoresis (PFGE) instrument in order to isolate the cleaved fragment as a distinct DNA band on the gel. Target bands (197 kb) from 5 lanes are cut out of the PFGE gel and DNA was recovered using GlAquick Gel Extraction kit (column), eluted with 15 ul elution buffer and tested the concentration on a Qubit instrument. The resulting sample contained ~0.426 ng/ul target DNA. A sequencing library was prepared using Truseq kit for library prep and the library was sequenced in a 150×2 miseq run as one of many samples in the lane. Sequencing resulted in 265386×2 reads and ~91 MGb×2 data in total, demonstrating the extremely deep coverage achievable for such a target region.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Cited in the Application

Endy, D. Foundations for engineering biology. *Nature* 438, 449-453, doi:10.1038/nature04342 (2005).

Keasling, J. D. Synthetic biology and the development of tools for metabolic engineering. *Metabolic engineering* 14, 189-195, doi:10.1016/j.ymben.2012.01.004 (2012).

Cobb, R. E. & Zhao, H. Direct cloning of large genomic sequences. *Nature biotechnology* 30, 405-406, doi: 10.1038/nbt.2207 (2012).

Gronenberg, L. S., Marcheschi, R. J. & Liao, J. C. Next generation biofuel engineering in prokaryotes. *Current opinion in chemical biology* 17, 462-471, doi:10.1016/j.cbpa.2013.03.037 (2013).

Barnes, W. M. PCR amplification of up to 35-kb DNA with high fidelity and high yield from lambda bacteriophage templates. *Proceedings of the National Academy of Sciences of the United States of America* 91, 2216-2220 (1994).

Li, M. Z. & Elledge, S. J. SLIC: a method for sequence- and ligation-independent cloning. *Methods in molecular biology* 852, 51-59, doi:10.1007/978-1-61779-564-0_5 (2012).

Gibson, D. G. et al. Enzymatic assembly of DNA molecules up to several hundred kilobases. *Nature methods* 6, 343-345, doi:10.1038/nmeth.1318 (2009).

Zhang, H. B. et al. Construction of BIBAC and BAC libraries from a variety of organisms for advanced genomics research. *Nature protocols* 7, 479-499, doi:10.1038/nprot.2011.456 (2012).

Fu, J. et al. Full-length RecE enhances linear-linear homologous recombination and facilitates direct cloning for bioprospecting. *Nature biotechnology* 30, 440-446, doi: 10.1038/nbt.2183 (2012).

Yamanaka, K. et al. Direct cloning and refactoring of a silent lipopeptide biosynthetic gene cluster yields the antibiotic taromycin A. *Proceedings of the National Academy of Sciences of the United States of America* 111, 1957-1962, doi:10.1073/pnas.1319584111 (2014).

Wang, R. Y., Shi, Z. Y., Chen, J. C. & Chen, G. Q. Cloning Large Gene Clusters from E-coli Using in Vitro Single-Strand Overlapping Annealing. *Acs Synth Biol* 1, 291-295, doi:Doi 10.1021/Sb300025d (2012).

Jinek, M. et al. A programmable dual-RNA-guided DNA endonuclease in adaptive bacterial immunity. *Science* 337, 816-821, doi:10.1126/science.1225829 (2012).

Doudna, J. A. & Charpentier, E. Genome editing. The new frontier of genome engineering with CRISPR-Cas9. *Science* 346, 1258096, doi:10.1126/science.1258096 (2014).

Karvelis, T., Gasiunas, G. & Siksnys, V. Programmable DNA cleavage in vitro by Cas9. *Biochemical Society transactions* 41, 1401-1406, doi:10.1042/B5T20130164 (2013).

Kim, J. M., Kim, D., Kim, S. & Kim, J. S. Genotyping with CRISPR-Cas-derived RNA-guided endonucleases. *Nature communications* 5, 3157, doi:10.1038/ncomms4157 (2014).

Vargas-Bautista, C., Rahlwes, K. & Straight, P. Bacterial competition reveals differential regulation of the pks genes by Bacillus subtilis. *Journal of bacteriology* 196, 717-728, doi:10.1128/JB.01022-13 (2014).

Han, L., Yang, K., Ramalingam, E., Mosher, R. H. & Vining, L. C. Cloning and characterization of polyketide synthase genes for jadomycin B biosynthesis in Streptomyces venezuelae ISP5230. *Microbiology* 140 (Pt 12), 3379-3389 (1994).

Vanek, Z., Cudlin, J., Blumauerova, M. & Hostalek, Z. How many genes are required for the synthesis of chlortetracycline? *Folia microbiologica* 16, 225-240 (1971).

Hsu, P. D. et al. DNA targeting specificity of RNA-guided Cas9 nucleases. *Nature biotechnology* 31, 827-832, doi:10.1038/nbt.2647 (2013).

Ran, F. A. et al. Double Nicking by RNA-Guided CRISPR Cas9 for Enhanced Genome Editing Specificity. *Cell* 154, 1380-1389, doi:DOI 10.1016/j.cell.2013.08.021 (2013).

What is claimed is:

1. A method of fragmenting mammalian or plant DNA, the method comprising:
   (a) providing a semi-solid biological sample which comprises lysed mammalian or plant cells in an agarose gel; and
   (b) contacting said semi-solid biological sample with Cas9 clease and an RNA oligonucleotide- having a binding affinity and selectivity to pre-defined sites in the mammalian or plant DNA of said lysed mammalian or plant cells under conditions which allow sufficient enzyme diffusion in said agarose gel in the absence of pulsed-field gel electrophoresis and hybridization of the RNA oligonucleotide to the mammalian or plant DNA, so as to digest said mammalian or plant DNA and yield a DNA fragment-of-interest, wherein said fragment of interest is 50-200 kb in length.

2. The method of claim 1, wherein said DNA is genomic DNA.

3. The method of claim 2, wherein said DNA is chromosomal DNA.

4. The method of claim 1, wherein said DNA is human DNA.

5. The method of claim 1, wherein said semi-solid biological sample prevents DNA shearing.

6. The method of claim 1, further comprising separating the DNA fragment-of-interest from the mammalian or plant DNA following step (b).

7. The method of claim 6, wherein said separating the DNA fragment-of-interest comprises pulsed-field gel electrophoresis.

8. The method of claim 6, wherein said separating is effected by at least one of:
   (a) melting said semi-solid biological sample; and
   (b) subjecting said semi-solid biological sample to enzymatic treatment which digests a gel matrix of said semi solid biological sample.

9. The method of claim 1, wherein said semi-solid biological sample is in the form of a plug.

10. The method of claim 1, wherein said contacting is effected for two hours.

11. A method of fragmenting mammalian or plant DNA, the method comprising:
    (a) providing a semi-solid biological sample which comprises lysed mammalian or plant cells in an agarose gel of about 1%; and
    (b) contacting said semi-solid biological sample with Cas9 nuclease and an RNA oligonucleotide having a binding affinity and selectivity to pre-defined sites in the mammalian or plant DNA of said lysed mammalian or plant cells under conditions which allow sufficient Cas9 nuclease diffusion in said agarose gel in the absence of pulsed-field gel electrophoresis, so as to digest said mammalian or plant DNA and yield a DNA fragment-of-interest.

12. The method of claim 11, wherein said fragment of interest is 50-200 kb in length.

* * * * *